US012766040B2

(12) United States Patent
Friedman

(10) Patent No.: US 12,766,040 B2
(45) Date of Patent: Oct. 20, 2026

(54) ADHESIVE BANDAGE CAPABLE OF ADMINISTERING TEMPORARY TATTOO

(71) Applicant: Steven Avi Friedman, Concord, CA (US)

(72) Inventor: Steven Avi Friedman, Concord, CA (US)

( * ) Notice: Subject to any disclaimer, the term of this patent is extended or adjusted under 35 U.S.C. 154(b) by 303 days.

(21) Appl. No.: 18/183,362

(22) Filed: Mar. 14, 2023

(65) Prior Publication Data

US 2023/0285194 A1 Sep. 14, 2023

Related U.S. Application Data

(60) Provisional application No. 63/319,666, filed on Mar. 14, 2022, provisional application No. 63/398,010, filed on Aug. 15, 2022.

(51) Int. Cl.

| | |
|---|---|
| ***A61F 13/00*** | (2024.01) |
| ***A61F 13/02*** | (2024.01) |
| ***B41M 5/00*** | (2006.01) |

(52) U.S. Cl.

CPC .... *A61F 13/00059* (2013.01); *A61F 13/0266* (2013.01); *A61F 13/0289* (2013.01); *B41M 5/0076* (2013.01); *A61F 2013/00365* (2013.01)

(58) Field of Classification Search

CPC ...... A61B 2090/395; A61B 2090/3983; A61B 2090/3937; A61B 2090/3904; A61B 90/39; A61M 35/00; A61F 15/00; A61F 15/001; A61F 13/00; A61F 13/00021; A61F 13/00089; A61F 13/0266; A61F 13/00085; A61F 13/0243; A61F 13/0253; A61F 13/00059; A61F 13/00072; A61F 13/00076; A61F 13/0008; A61F 13/024; A61F 13/0246; A61F 13/025; A61F 13/0263; A61F 2013/00365; A61F 13/0289; A61F 13/02; B41M 5/0076; B41M 5/00

USPC .... 602/41–43, 54, 55, 79, 57; 604/304, 307; 606/116

See application file for complete search history.

(56) References Cited

U.S. PATENT DOCUMENTS

| | | | | |
|---|---|---|---|---|
| 5,958,560 | A * | 9/1999 | Ewan | G03G 7/0093 428/354 |
| 6,074,721 | A * | 6/2000 | Moore | B41M 3/12 606/186 |
| 6,106,852 | A * | 8/2000 | Vineberg | A61K 8/0208 428/914 |
| 6,264,786 | B1 * | 7/2001 | Cromett | B44C 1/1733 156/247 |
| 2009/0260567 | A1 * | 10/2009 | Ozuna | B44C 1/005 118/600 |
| 2012/0037291 | A1 * | 2/2012 | Goolishian | A61B 90/39 428/41.7 |
| 2015/0065937 | A1 * | 3/2015 | Nassos | A61F 13/00059 602/54 |
| 2017/0252221 | A1 * | 9/2017 | Scopelliti | A61F 13/00059 |

(Continued)

*Primary Examiner* — Caitlin A Carreiro

(74) *Attorney, Agent, or Firm* — West & Associates, A PC; Stuart J. West; Charlotte Rodeen-Dickert

(57) ABSTRACT

An adhesive bandage is combined with temporary tattoos. When the bandage is removed with water, a temporary tattoo is transferred to the skin. Some versions of the adhesive bandage can have a base strip, an adhesive layer, a pad, a protective strip and a temporary tattoo assembly, which has at least an ink layer and a release coating.

16 Claims, 29 Drawing Sheets

(56) References Cited

U.S. PATENT DOCUMENTS

| | | | | |
|---|---|---|---|---|
| 2019/0321233 | A1* | 10/2019 | Wallis | A61F 13/025 |
| 2023/0285195 | A1* | 9/2023 | Friedman | A61F 13/0259 |

* cited by examiner

ADHESIVE BANDAGE CAPABLE OF ADMINISTERING TEMPORARY TATTOO

CROSS-REFERENCE TO RELATED APPLICATION(S)

This application claims the benefit of priority to prior-filed and provisional patent application Ser. No. 63/319,666, filed Mar. 14, 2022, by Steven Avi Friedman and provisional patent application Ser. No. 63/398,010, filed Aug. 15, 2022, by Steven Avi Friedman, the entireties of each of which are hereby incorporated herein by reference.

BACKGROUND

Technical Field

The present device relates to the field of medical wound care, particularly adhesive bandages.

Background

Children often cut and scrape themselves, resulting in small open wounds. The typical treatment for these types of wounds is to place an adhesive-backed protective bandage over the injured area. This bandage protects the wound from the outside environment, allowing it to heal properly. Unfortunately, children are often fearful of wearing adhesive-backed wound bandages due to the potential pain that occurs when the sticky bandage is peeled off the wearer's skin (bandage removal). The fear of this experience can lead to the child either not wearing a bandage altogether (non-compliance), thereby risking infection, or wearing the bandage but enduring stress both in anticipation of the bandage removal and during the actual bandage removal process.

However, children love temporary tattoos that are transferred to the skin by applying water. An adhesive-backed bandage that also left a temporary tattoo behind after removal, would help children look forward to the bandage removal step. Moreover, the temporary tattoo requires the user to soak the bandage as part of the transfer process. This soaking process doubles to weaken the adhesive bond to the child's skin, thereby making the overall removal step considerably less painful.

What is needed is a product that combines an adhesive bandage with a temporary tattoo that allows children to wear adhesive-backed wound bandages without the fear of painful removal. A positive bandage-removal experience stands to drive greater compliance (and therefore improved wound treatment) while also reducing stress for both parent and child.

SUMMARY

An adhesive-backed bandage can protect the wound for proper healing but also transfer a temporary tattoo to the child's skin during removal. Children enjoy temporary tattoos, and therefore incorporating this technology into a bandage ensures the child is incentivized to wear the bandage and excited for the bandage removal process. Moreover, transferring the temporary tattoo requires the user to soak the bandage with water. This soaking step doubles to also weaken the bandage adhesive's bond to the child's skin, thereby making the bandage removal process (peeling the bandage off) considerably less painful. The combination of these factors stands to make the bandage removal a significantly more positive experience for the child.

BRIEF DESCRIPTION OF THE DRAWINGS

Further details of the present device are explained with the help of the attached drawings in which.

DETAILED DESCRIPTION

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Figure 1A:
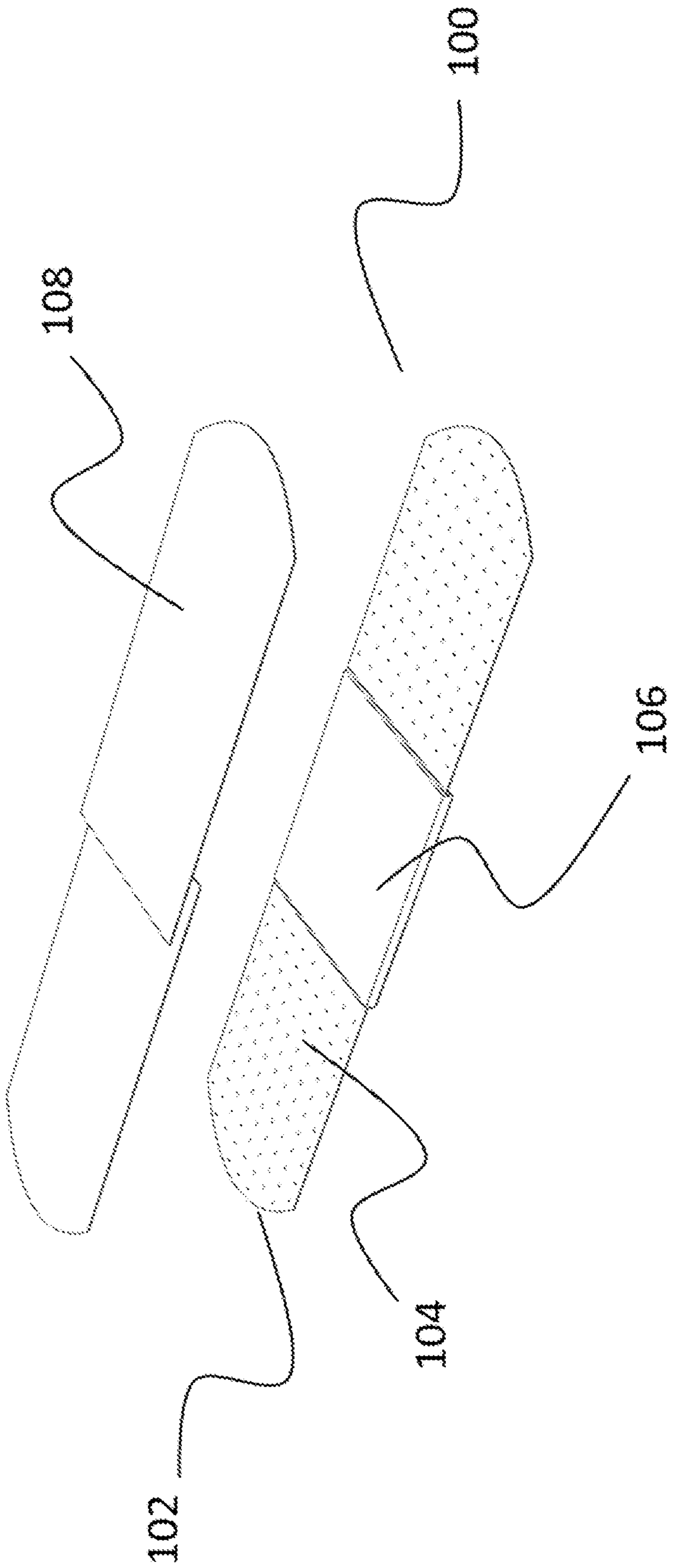
FIG. 1*a* depicts a perspective view of a bandage assembly embodiment of the present device.

FIG. 1*a* depicts a perspective view of a bandage assembly embodiment of the present device. In some embodiments, an adhesive bandage assembly 100 can comprise a base strip 102. A base strip 102 can be comprised of a polymer, fabric, elastomeric, or any other known, convenient and/or desired material. In some embodiments, an adhesive layer 104 can be applied to one side of a base strip 102. A pad 106 can be placed substantially at the center point of a base strip 102. In some embodiments, a pad 106 can have a rectangular geometry, but in other embodiments can have any other known, convenient and/or desired geometry. A pad 106 can be comprised of a soft fabric, gauze, a polymer, or any other known, convenient and/or desired material. A removable protective strip 108 can be placed adjacent to an adhesive layer 104. In some embodiments, a removable protective strip 108 can be split into two overlapping pieces, but in other embodiments can be a singular strip or two non-overlapping pieces. A removable protective strip 108 can be comprised of a polymer or coated paper such that it can be easily removed from an adhesive layer 106 or any other known, convenient and/or desired material.

Figure 1B:
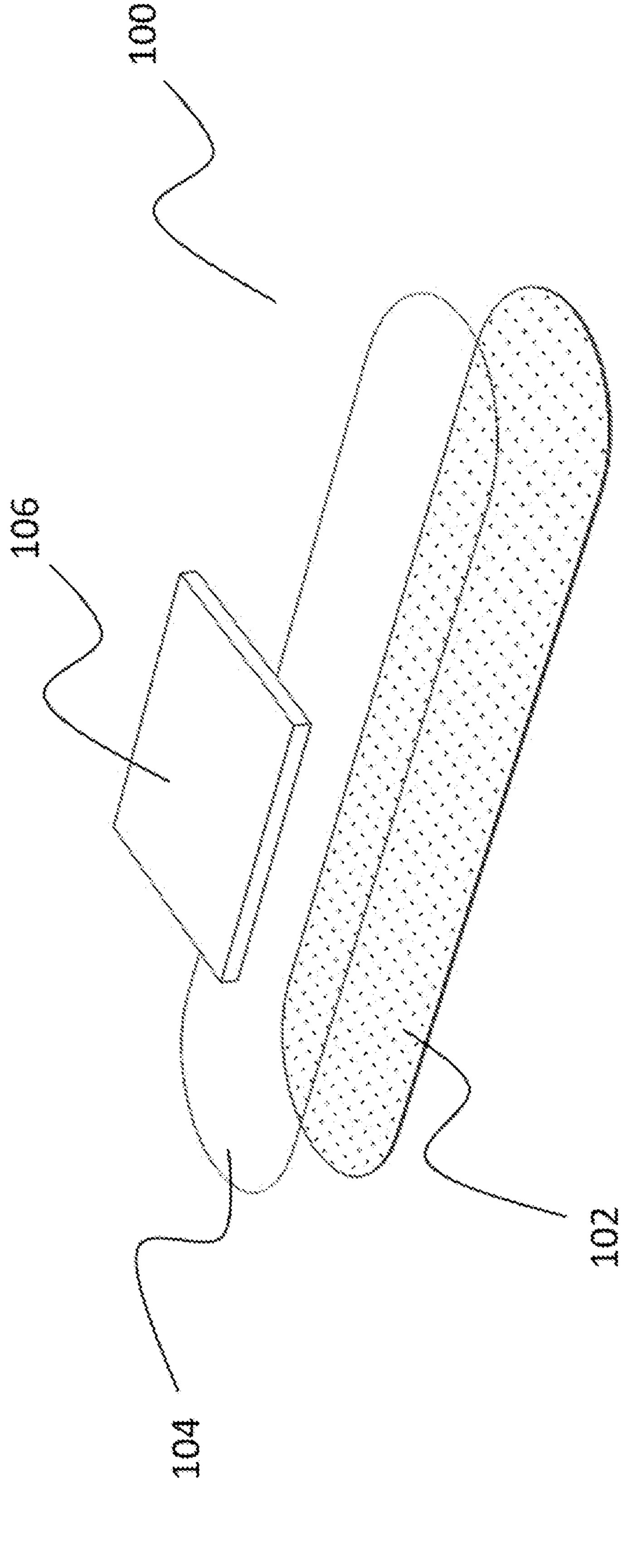
FIG. 1*b* depicts a detail perspective assembly view of the bandage assembly shown in FIG. 1*a*.

FIG. 1*b* depicts a detail perspective assembly view of the bandage assembly shown in FIG. 1*a*. As shown in FIG. 1*b*, an adhesive layer 104 can substantially cover a surface of a base strip 102. In some embodiments, a pad 106 can be applied directly to an adhesive layer 104.

Figure 2:
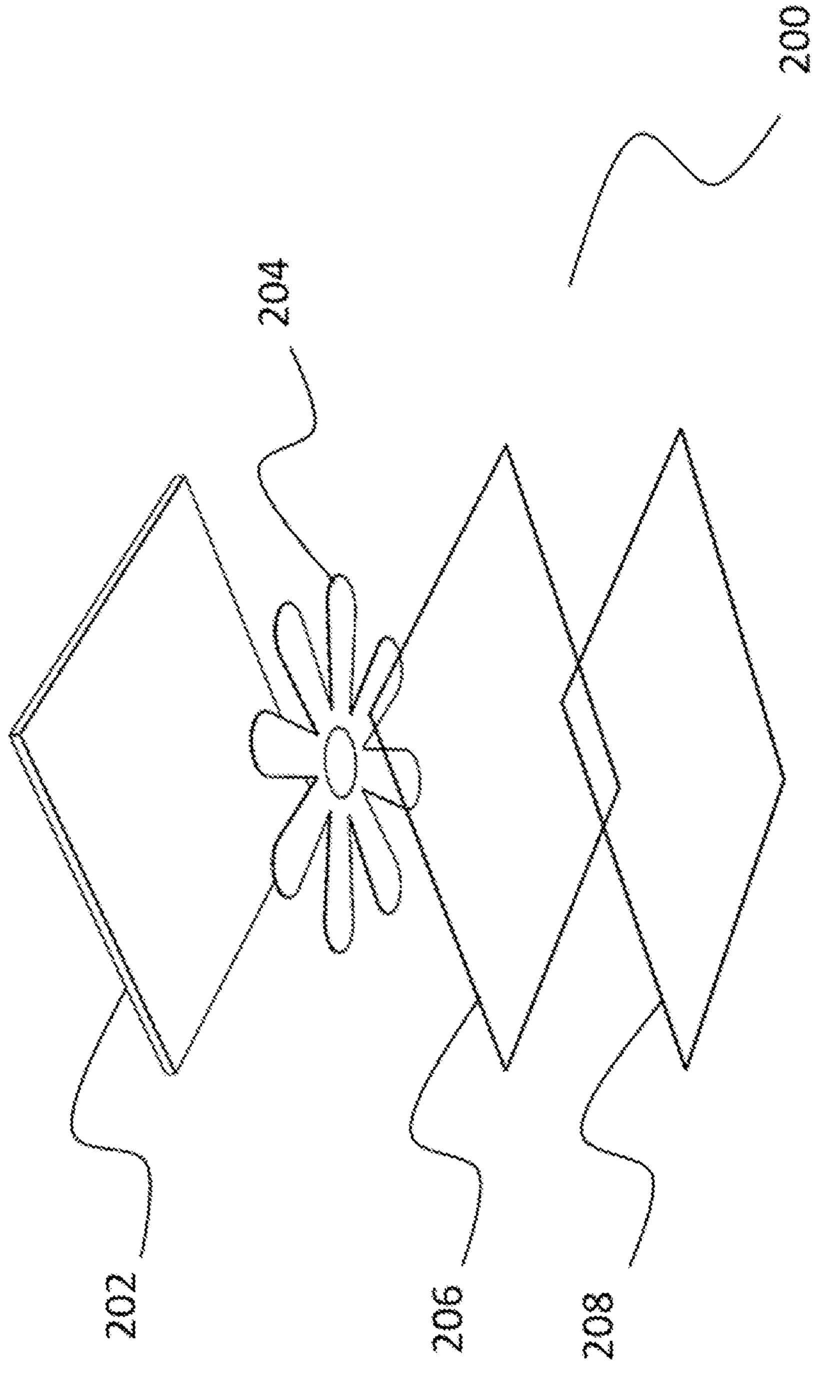
FIG. 2 depicts a perspective assembly view of a tattoo assembly embodiment of the present device.

FIG. 2 depicts a perspective assembly view of a temporary tattoo assembly embodiment of the present device. As shown in FIG. 2, a temporary tattoo assembly 200 can have a cover layer 202. In some embodiments, a cover layer 202 can be comprised of a polymer, coated paper, or any other known, convenient and/or desired material. In such embodiments, a cover layer 202 can be a removable protective strip 108 and the ink layer 204 is separable from the cover layer 202. An ink layer 204 can be adapted and configured to temporarily adhere to skin. In some embodiments, there can be an adhesive layer 104 (not shown) between ink layer 204 and cover layer 202 to further aid adhesion between the ink layer 204 and the skin. In some embodiments, an ink layer 204 can be an image, pattern, or any other known, convenient and/or desired graphic. In some embodiments, a transfer film 206 can be in direct contact with at least a portion of the ink layer 204. In some alternate embodiments, a release coating 208 can be in direct contact with at least a portion of the transfer film 206. In some embodiments, release coating 208 and transfer film 206 can be in any known, convenient and/or desired order and/can be combined as a single layer. In some embodiments, temporary tattoo assembly 200 can comprise a water or liquid permeable backing layer (later referenced as 702) comprised of a polymer, paper, or any other known, convenient and/or desired material opposite the cover layer 202, such that the ink layer 204, transfer layer 206, and release coating 208 are positioned between backing layer 702 and a cover layer 202.

Figure 3:
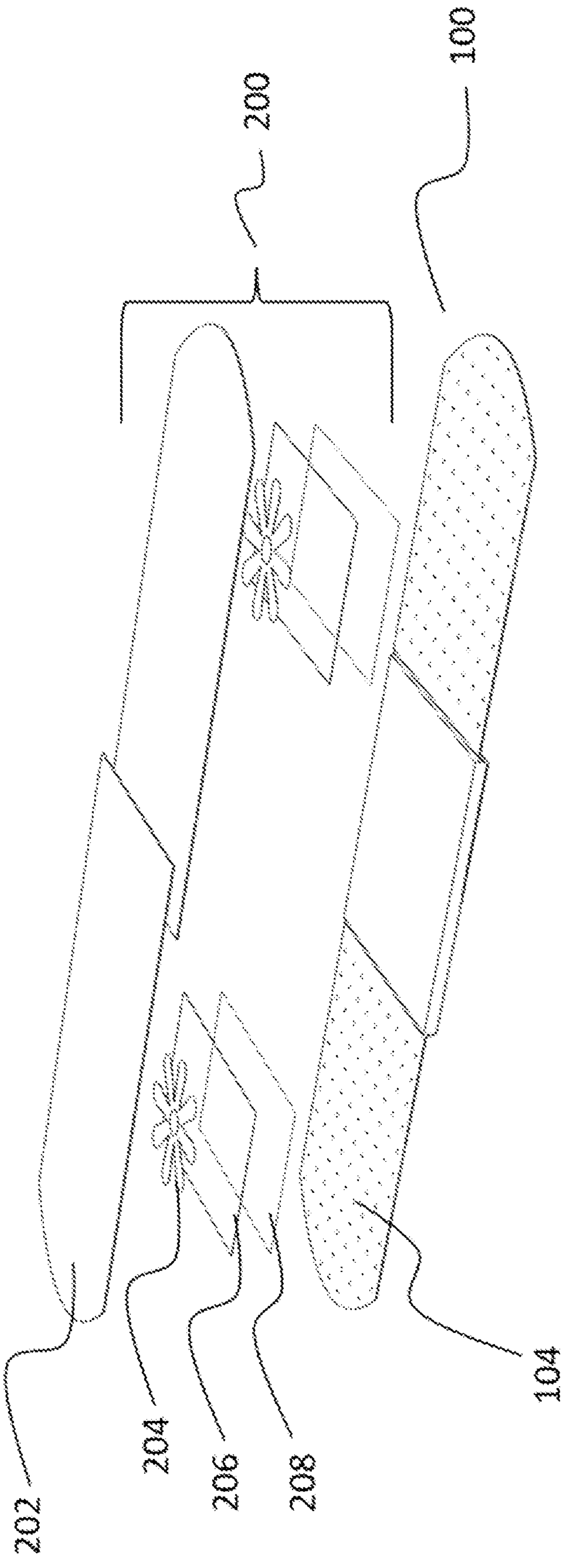
FIG. 3 depicts a perspective assembly view of an embodiment of the present device.

FIG. 3 depicts a perspective assembly view of an embodiment of the present device. As shown in FIG. 3, at least one tattoo assembly 200 can be added to a bandage assembly 100. In some embodiments a cover layer 202 can be the protective strip 108. In such embodiments, an ink layer 204 can be adjacent to a surface of a cover layer 202. A transfer film 206 can be in direct contact with at least a portion of an ink layer 204. A release coating 208 can be in direct contact with at least a portion of a transfer film 206. The outer surface of a release coating 208 can be in direct contact with at least a portion of an adhesive layer 104 of an adhesive bandage assembly 100.

Figure 4:
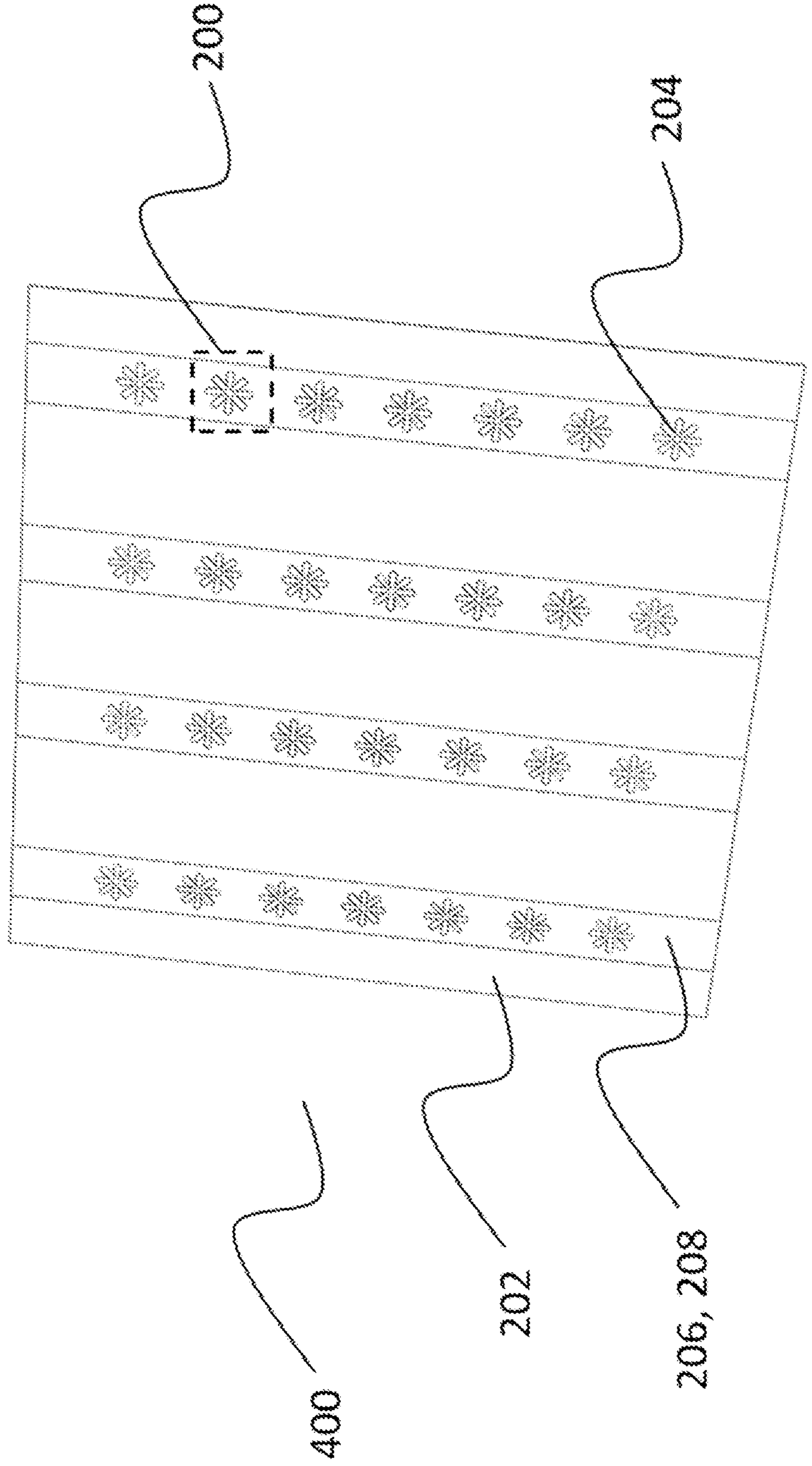
FIG. 4 depicts a perspective view of an embodiment of a backing material sheet of the present device.

FIG. 4 depicts a perspective view of an embodiment of a protective material sheet 400 of the present device. A protective material sheet 400 can be provided to cut smaller protective strips 108 from the larger sheet. In some embodiments, the sheet 400 can be in roll form and can selectively function with machinery such as a rotary die cutter. In some embodiments temporary tattoos can be integrated with adhesive bandages by replacing the existing layers of protective strip 108 material with sheets of cover layer 202 material that can comprise columns of at least one ink layer 204, at least one transfer layer 206, and/or a release coating 208. In such embodiments, the embodiments can be adapted and configured such as not to change or interfere with the manufacturing of the actual adhesive bandage. In some embodiments, a manufacturer can replace the sheet used for protective strips 108 with protective sheet 400. In operation, a temporary tattoo assembly 200, wherein the cover layer 202 can be shaped as a protective strip 108, can be an exact replacement for standard protectives strips 108. In some embodiments, temporary tattoo elements ink layer 204, transfer layer 206, and release coating 208 can be selectively applied directly to a sheet of cover layer 202 material in a column configuration. In other embodiments, temporary tattoo elements ink layer 204, transfer layer 206, and release coating 208 can be applied directly to sheets of protective strip 108 material in a column configuration. As shown in FIG. 4, a sheet 400 can comprise cover layer 202 material configured with columns of release coating 208, at least one transfer layer 206, and/or at least one ink layer 204 applied directly on or otherwise coupled with its surface. In other embodiments, a temporary tattoo assembly 200 can be constructed as a stand-alone subassembly, and then adhered to a protective strip 108 material as a secondary process.

Figure 5:
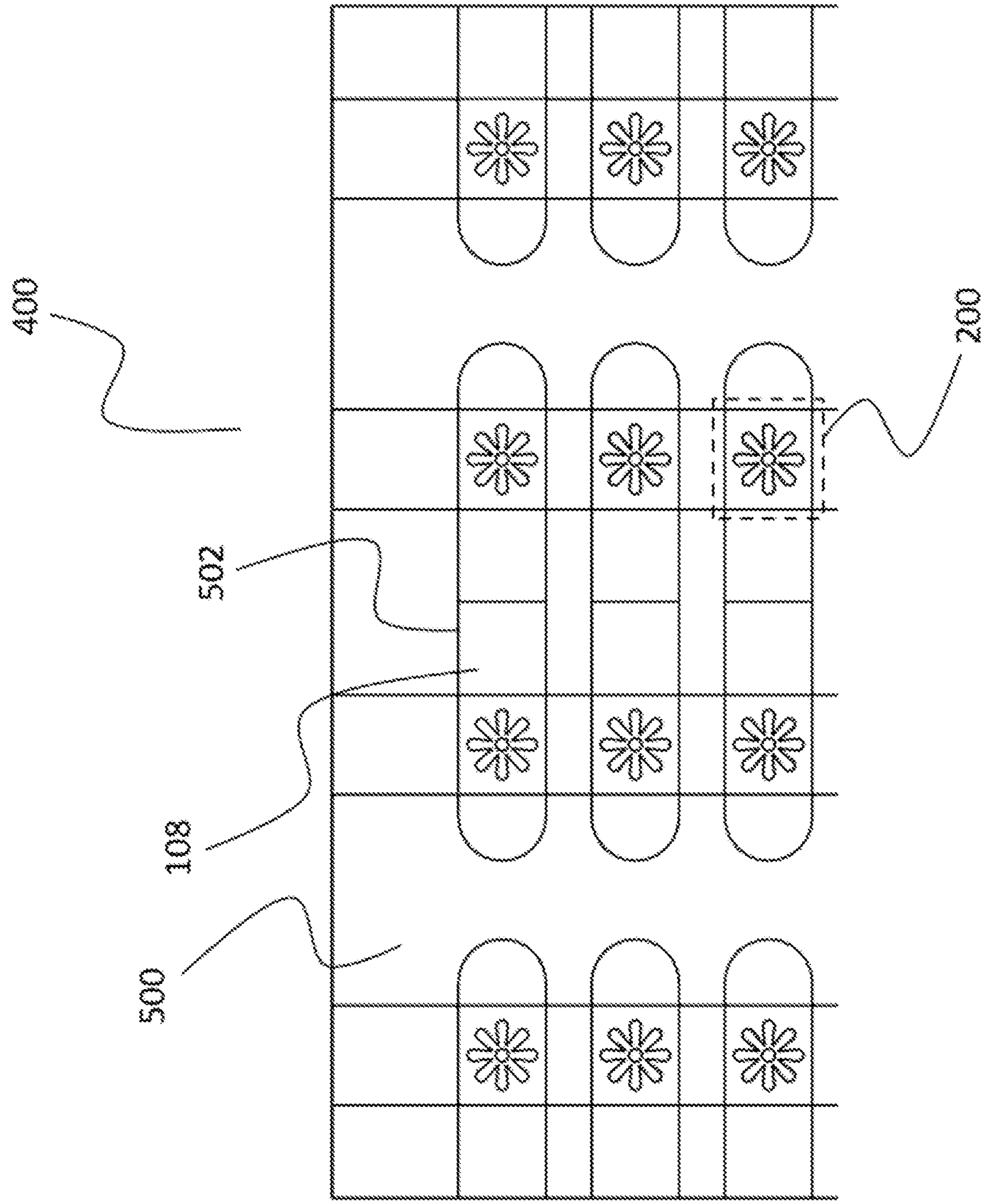
FIG. 5 depicts a planar view of an embodiment of cutting patterns for bandages in the present device.

FIG. 5 depicts a planar view of an embodiment of cutting patterns for bandage protective strips 108 in the present device. In some embodiments protective strips 108 and/or tattoo assemblies 200 can comprise a flap cutting pattern 502 cut from sheet 400 to selectively engage with an adhesive layer 104 of a bandage assembly 100. In some embodiments, the sheet backing material 500 can be comprised of either tattoo cover material 202, standard and/or known protective backing material 108, or similar materials, configured in columns of ink layer 204, at least one transfer layer 206, and/or a release coating 208 added. The larger sheet 400 can be cut into smaller pieces to fit with a desired final adhesive bandage size.

Figure 6A:
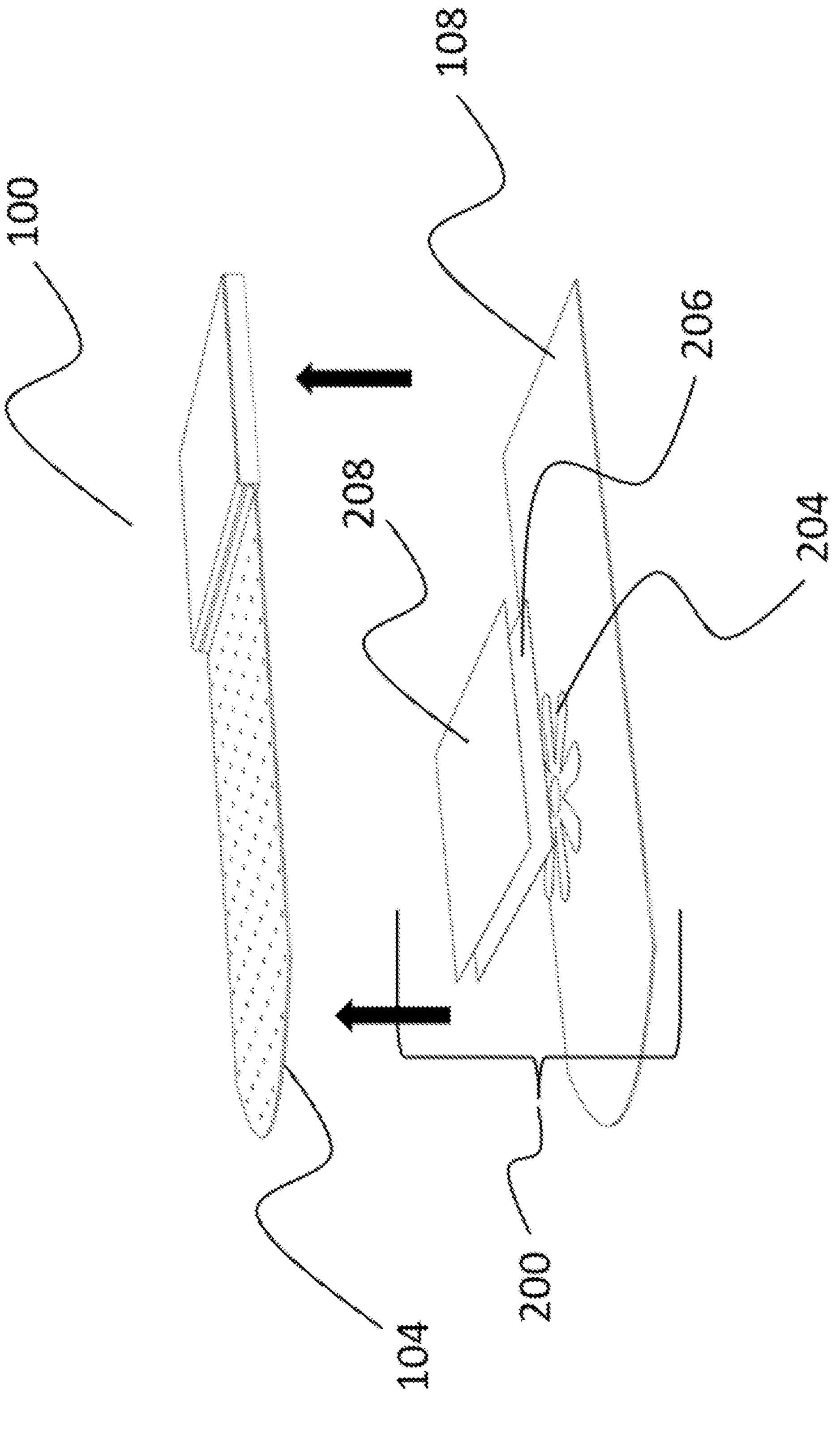
FIG. 6*a* depicts a detailed perspective assembly view of the present device prior to use.

FIG. 6*a* depicts a detailed perspective assembly view of the present device prior to use. As shown in FIG. 6*a*, a tattoo assembly 200 can comprise a backing strip 108 comprised of either tattoo cover material 202 or backing strip material 108, at least one ink layer 204, at least one transfer layer 206, and/or a release coating 208. When the tattoo assembly 200 is assembled to form the bandage 100, the tattoo elements and the adhesive layer 104 can be protected before use.

Figure 6B:
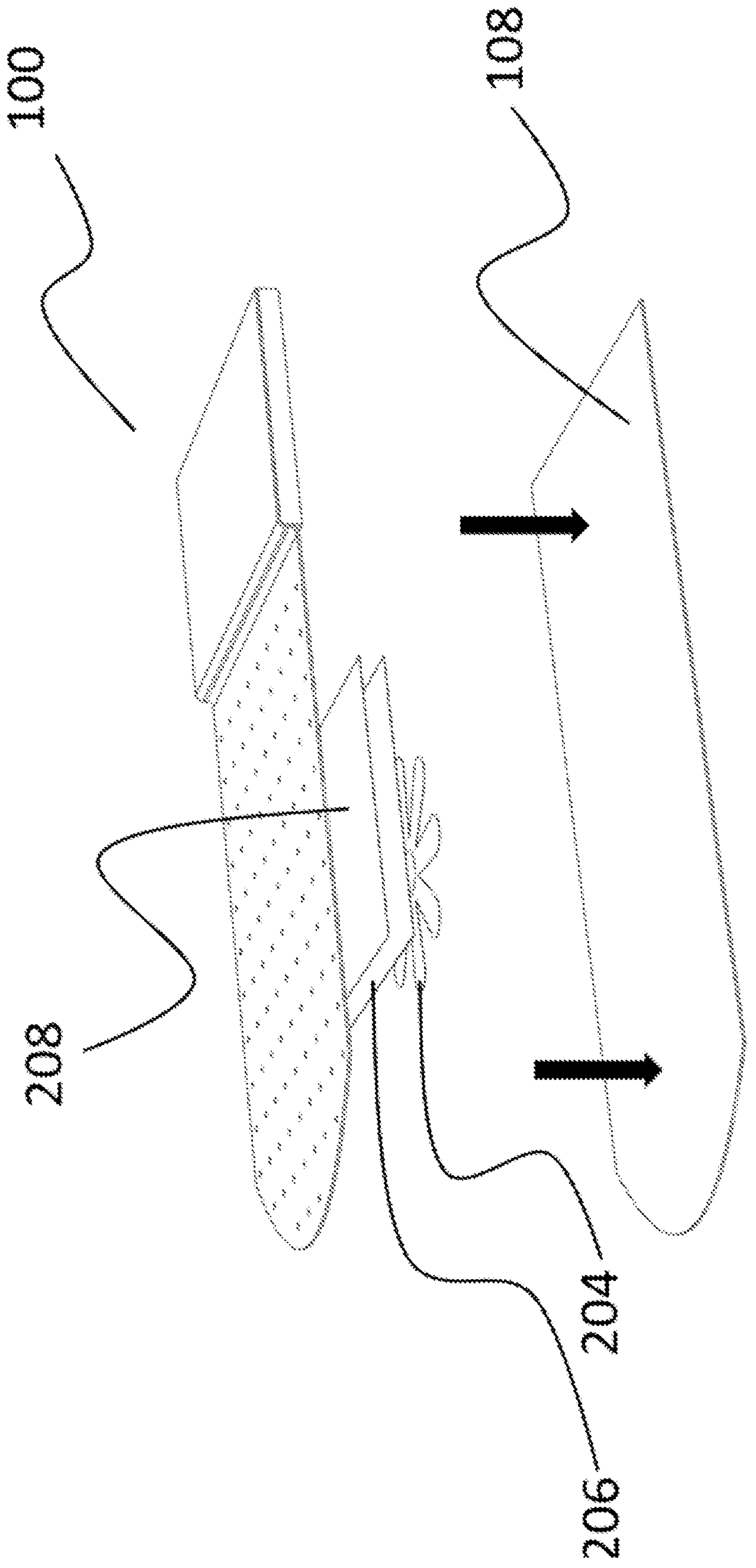
FIG. 6*b* depicts a detailed perspective assembly view of the present device prior to application on a user.

FIG. 6*b* depicts a detailed perspective assembly view of the present device as it can be applied on a user. A backing strip 108 can be removed, exposing an ink layer 204, transfer film 206, and release layer 208 on an adhesive layer 104. In use, a bandage can be applied to the skin, such that an ink layer 204 can be in direct contact with the skin and covered by a transfer film 206 and a release coating 208 under a bandage 100.

Figure 6C:
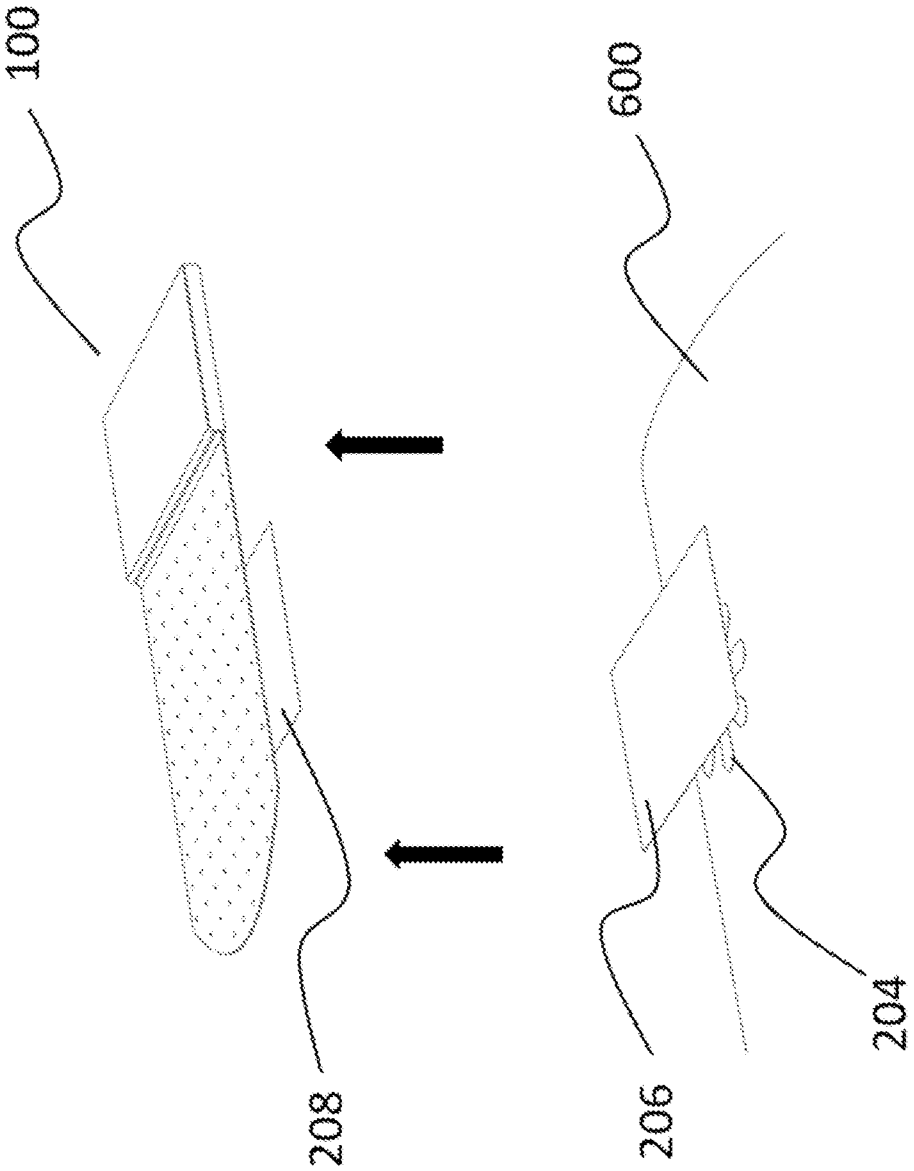
FIG. 6*c* depicts a detailed perspective assembly view of the present device after application on a user.

FIG. 6*c* depicts a detailed perspective assembly view of the present device after application on a user. Removing a bandage 100 can transfer a temporary tattoo comprised of an ink layer 204 and/or a transfer film 206. When a bandage 100 is on the wearer's skin, water and slight pressure can be applied to a bandage 100, such that a release coating 208 facilitates a transfer film 206 and an ink layer 204 to separate from a bandage 100 and adhere to skin 600. An ink layer 204 and/or transfer film 206 can then remain on skin for any known, convenient and/or desired duration after a bandage 100 is removed. In some embodiments, the transfer film 206 can remain wholly or partially with the bandage 100, and only the ink layer 204 can be wholly transferred to the skin. In some embodiments, the release coating 208 can partially or wholly transfer with the transfer film 206 to the user's skin. In some embodiments, an adhesive layer 704 can be included between the ink layer 204 and the skin 600 to help adhere the ink layer 204 to the skin.

Figure 7A:
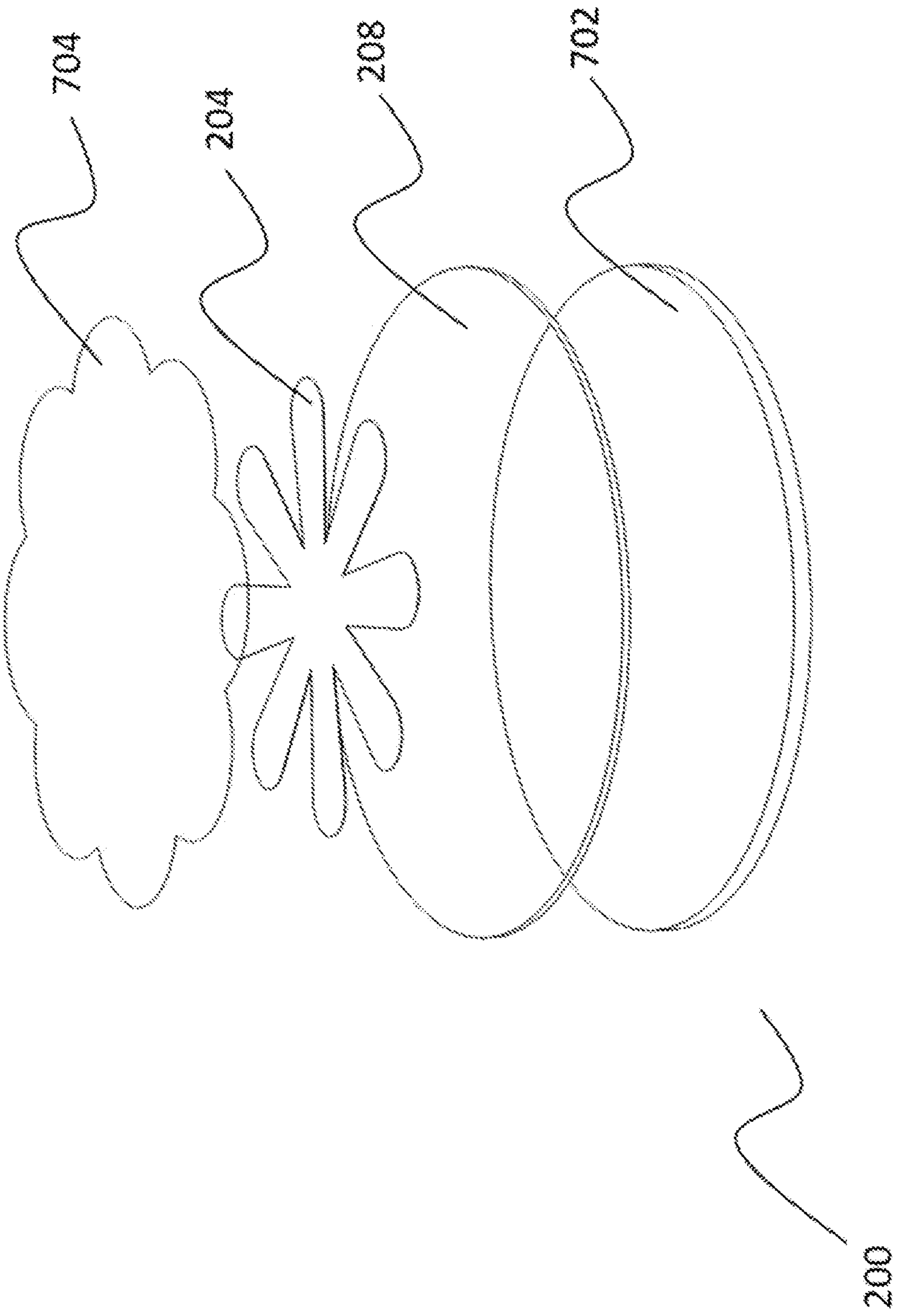
FIG. 7*a* depicts a detailed perspective assembly view of an alternative embodiment of a tattoo assembly of the present device.

FIG. 7*a* depicts a detailed perspective assembly view of an alternative embodiment of a tattoo assembly 200 of the present device. A temporary tattoo assembly 200 can be comprised of at least a paper (or other known, convenient and/or desired material) backing layer 702, a release coating layer 208, at least one ink layer 204, and/or a double-sided adhesive layer 704. In such embodiments, a paper backing layer 702 can be positioned onto a bandage adhesive layer 104 to integrate a bandage assembly 100 and a temporary tattoo assembly 200. In some embodiments, a release coating layer 208 can be combined with or be positioned adjacent to a transfer film 206 (not shown). Transfer layer 206 can help facilitate the ink layer 204 and the adhesive layer 704 cleanly and fully transferring to skin 600. In some embodiments, paper backing layer 702 can be permeable to water and/or any other known convenient and/or desired liquid. As will be readily apparent to one of ordinary skill in the art, a backing layer 702 can be comprised of alternative water and/or liquid permeable material, such as, but not limited to a water/liquid permeable polymer(s), fabric, elastomeric, or any other known, convenient and/or desired material.

Figure 7B:
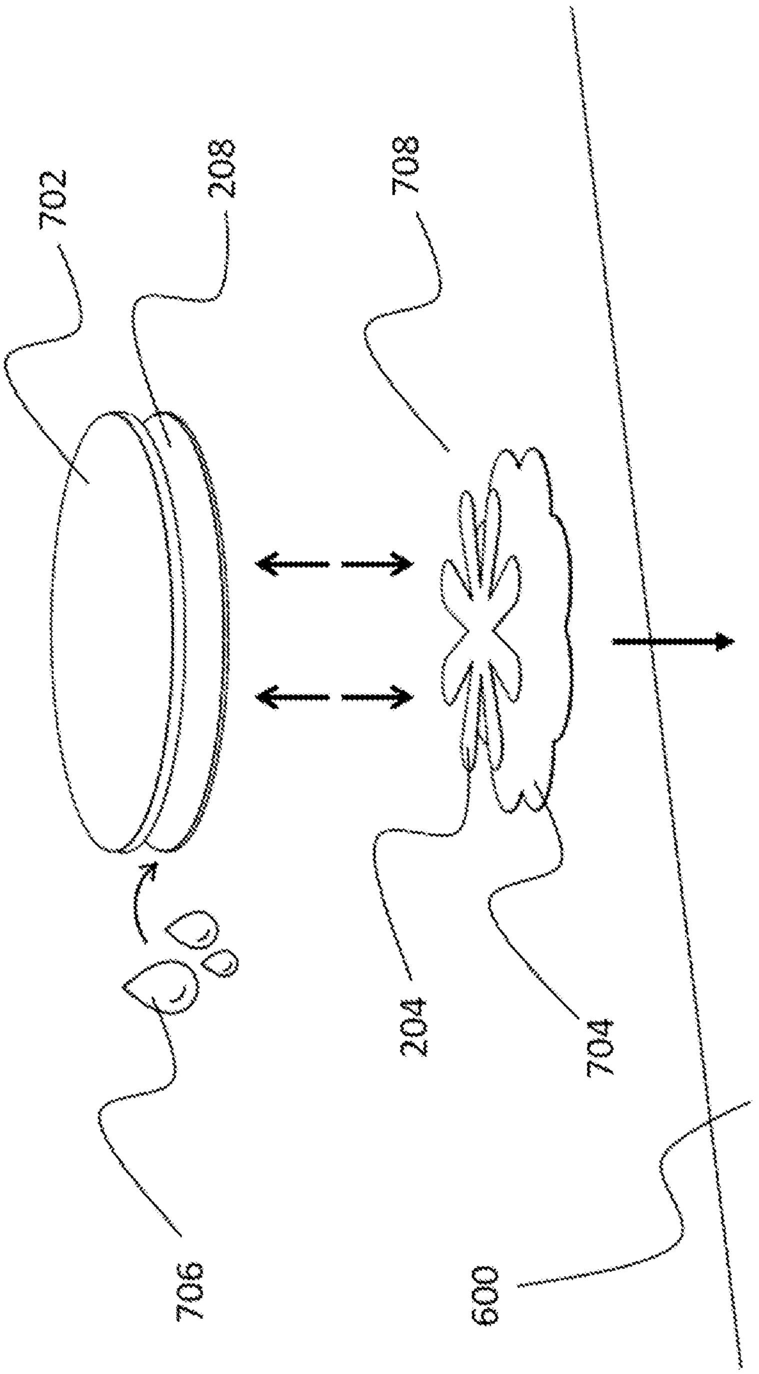
FIG. 7*b* depicts a detailed perspective assembly view of the embodiment shown in FIG. 7 in use.

FIG. 7*b* depicts a detailed perspective assembly view of the embodiment shown in FIG. 7*a* in use. As shown in FIG. 7*b*, when a release coating layer 208 can be saturated with water 706 (or any other known, convenient and/or desired liquid), it can transition into a slippery state such that an ink layer 204 and an adhesive layer 704 no longer adhere to it. As a result, an ink layer 204 and double-sided adhesive layer 704 can then be separated from a release coating layer 208 (and therefore also paper backing layer 702).

Furthermore, as shown in FIG. 7*b*, while an ink layer 204 and an adhesive layer 704 can be separable from a release coating layer 208 and a paper backing layer 702, an ink layer 204 and an adhesive layer 704 can still be adhered to each other, and both layers 204 and 704 adhered together can comprise the actual temporary tattoo image transfer subassembly 708. Moreover, the side of an adhesive layer 704 that can be positioned opposite an ink layer 204 can be used to attach a temporary tattoo image transfer subassembly 708 to various objects, including but not limited to a user's skin 600.

In other embodiments, it will be readily apparent to one of ordinary skill in the art that temporary tattoo assemblies and temporary tattoo image transfer subassemblies can comprise additional films, layers, and adhesives to aid in the transfer, durability, and manufacturability of the temporary tattoo. Moreover, it will be readily apparent to one of ordinary skill in the art how these layers can be arranged in different orders and relative sizes.

Figure 8:
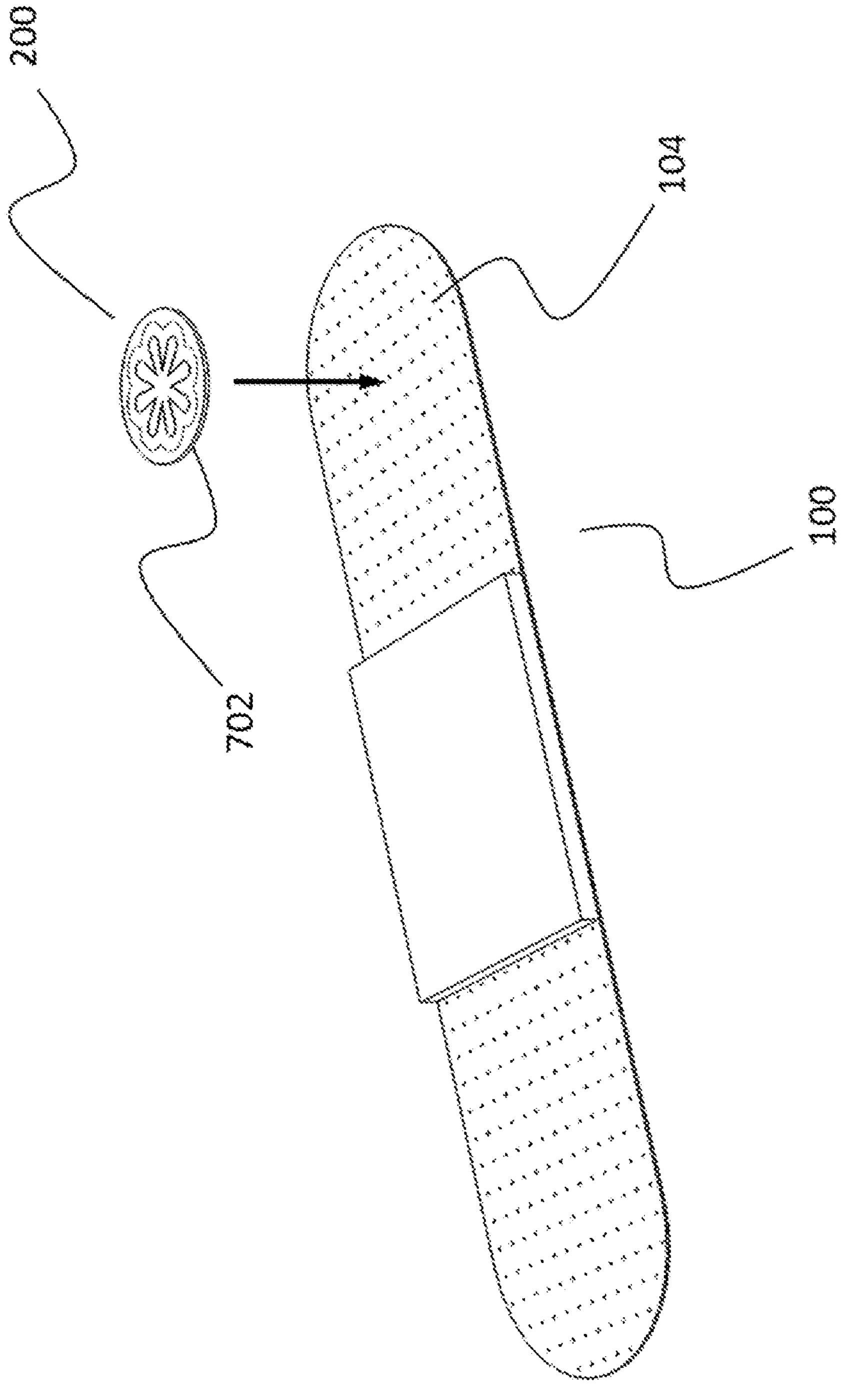
FIG. 8 depicts a detailed perspective assembly view of another embodiment of the present device.

FIG. 8 depicts a detailed perspective assembly view of another embodiment of the present device. As an alternative embodiment, the stand-alone temporary tattoo assembly 200 as described in FIG. 7*a* can be added directly to an adhesive layer 104 of a bandage 100 instead of a backing strip 108. In such embodiments, a paper backing layer 702 can be in direct contact with an adhesive layer 104.

Figure 9:
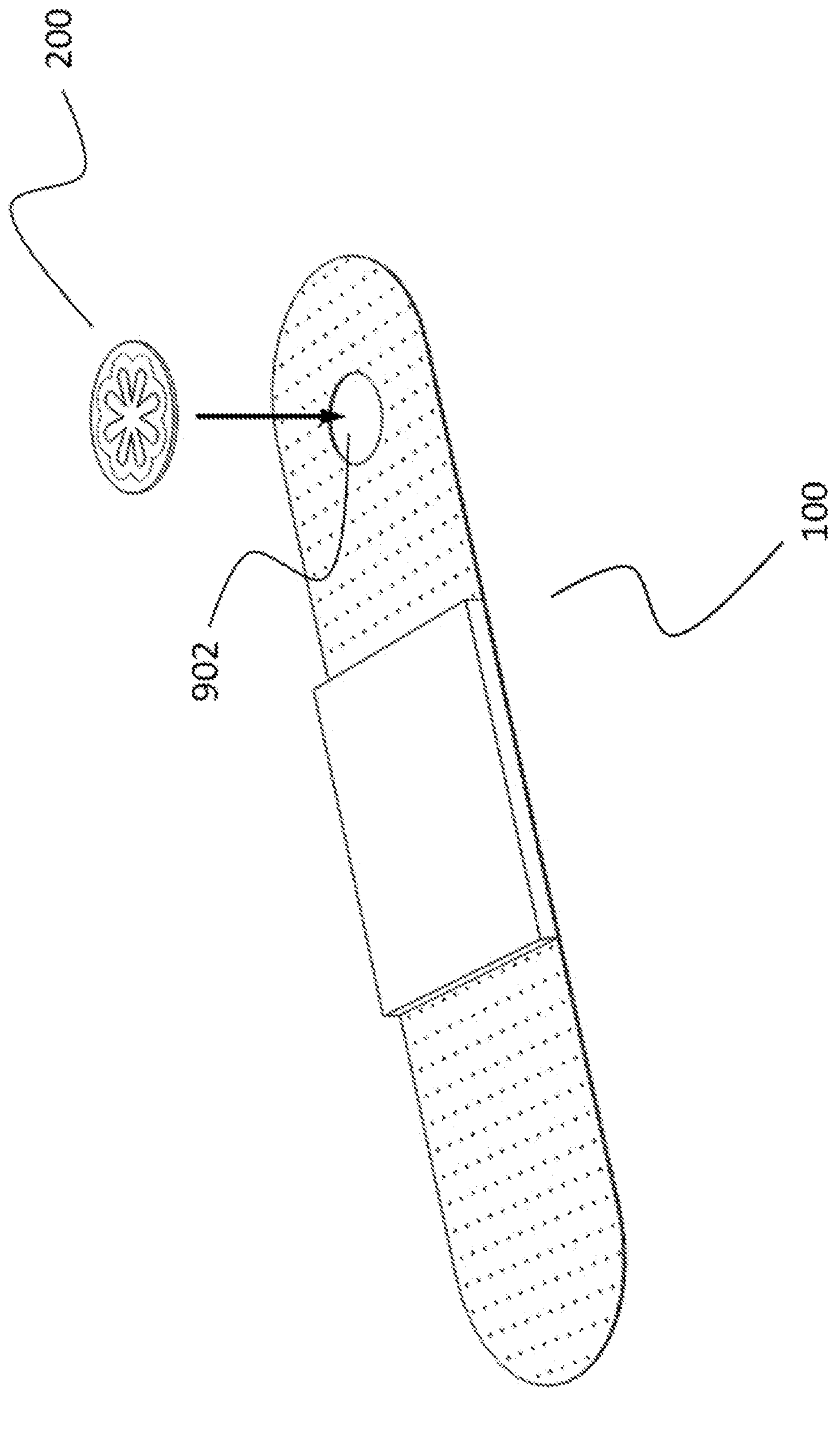
FIG. 9 depicts a detailed perspective assembly view of another embodiment of the present device.

FIG. 9 depicts a detail perspective assembly view of another embodiment of the present device. It is desirable that water and/or any other known, convenient and/or desirable liquid to access and penetrate the temporary tattoo release coating layer 208 to facilitate the temporary tattoo image transfer subassembly 708 separation from the larger temporary tattoo assembly 200 and transfer to a user's skin. However, in some embodiments, it may be desirable that a base strip 102 be waterproof to protect the wound from liquids. Moreover, in some embodiments it may be desirable for a bandage adhesive layer 104 to create a water-tight seal with a user's skin to protect the wound from liquids. In such situations, the alternative embodiment shown in FIG. 9 can enable water or liquid to access the release coating layer 208 despite base strip 102 and/or bandage adhesive layer 104 creating water-tight seals. In such embodiments, at least one cutout 902 can be added to a bandage assembly 100 substantially directly adjacent to a temporary tattoo assembly 200. As shown in FIG. 9, a cutout 902 can be substantially circular, but in other embodiments can have any other known, convenient and/or desired geometry. In such embodiments, a temporary tattoo assembly 200 can placed on top of a cutout 902, with a paper backing layer 702 adhering to a bandage adhesive layer 104.

Figure 10:
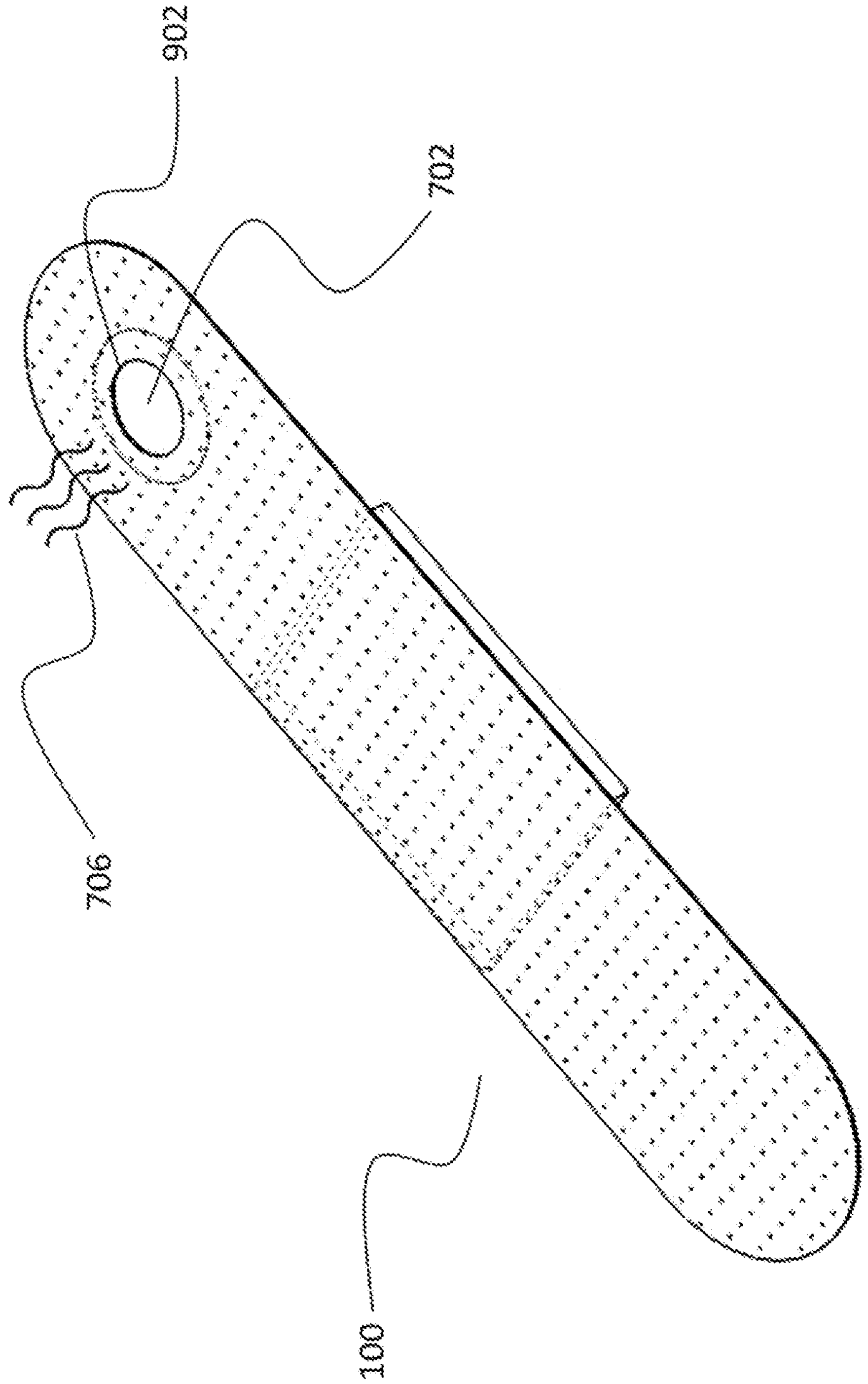
FIG. 10 depicts another perspective view of the of the embodiment shown in FIG. 9.

FIG. 10 depicts another perspective view of the of the embodiment shown in FIG. 9. As shown in FIG. 10, a cutout 902 can enable water or liquid 706 to access a paper backing 702. The water can penetrate a paper backing 702 via a cutout 902 to eventually seep through a paper backing layer 702 to wet a release coating 208. In such embodiments, when a bandage 100 is removed, paper backing 702 and release coating 208 remain attached to bandage 100 while the temporary tattoo image transfer subassembly 708 remains attached to the skin 600. The water 706 can penetrate a paper backing 702 via a cutout 902 and eventually seep through a paper backing 702 to wet a release coating layer 208 underneath, thereby freeing a temporary tattoo image transfer subassembly 708 to transfer to a user's skin 600.

In some embodiments, slicing and/or puncturing a bandage 100 alone may not provide sufficient water access for robust and reliable temporary tattoo transferring. In such cases, a larger cutout 902 can be created, where cutout diameters can be in the range of 4 mm±3 mm, or any other known, convenient and/or desired diameter.

Figure 11A:
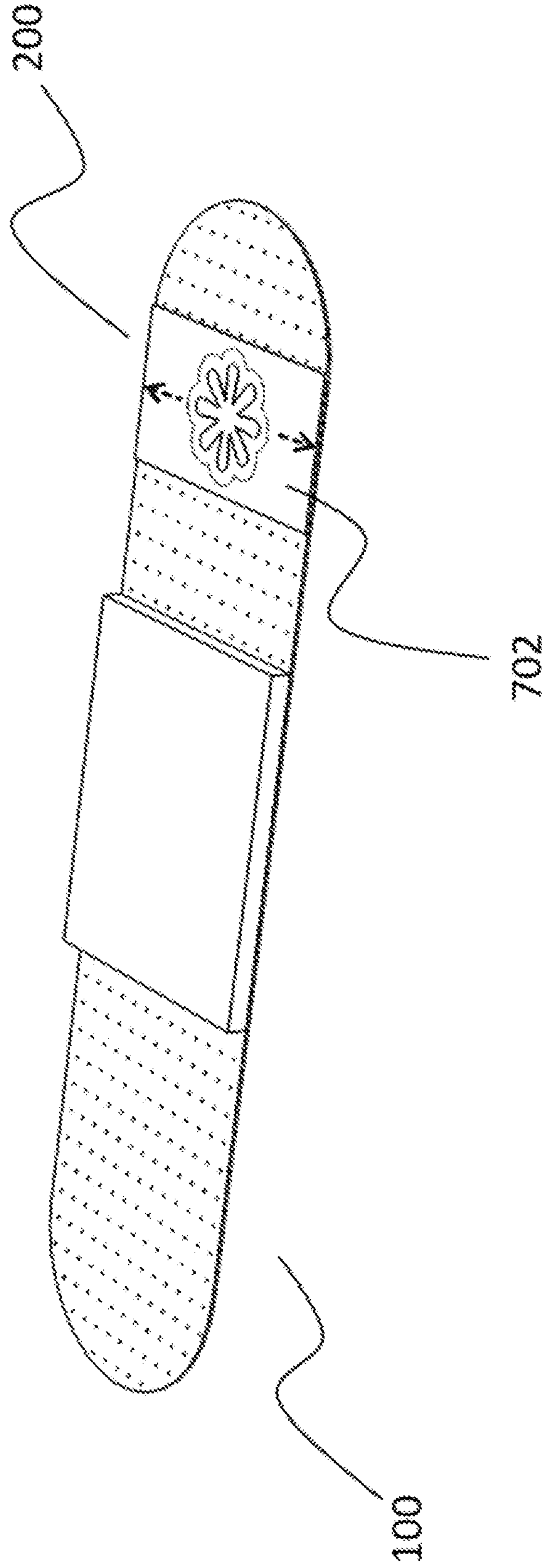
FIG. 11*a* depicts another embodiment of the present device.

FIG. 11*a* depicts another embodiment of the present device. There can be instances in which it is desirable to provide a water pathway to the release coating layer 208 without altering or adding cutouts 902 to a standard bandage assembly 100. The reasons for this can include, but are not limited to, ease of manufacturing, business strategy, and cost reduction. In some embodiments, water and/or any known, convenient and/or desired liquid can access a release coating layer 208 without impacting or substantially impacting a bandage assembly 100 by changing the shape of a paper backing layer 702 and release coating layer 208. In such embodiments, a paper backing layer 702 and release layer 208 can extend to the edges of a bandage 100. This embodiment can facilitate breaking the adhesive border between a bandage 100 and a user's skin 600, thereby creating a water and/or liquid ingress point through the paper backing 702 wall thickness.

Figure 11B:
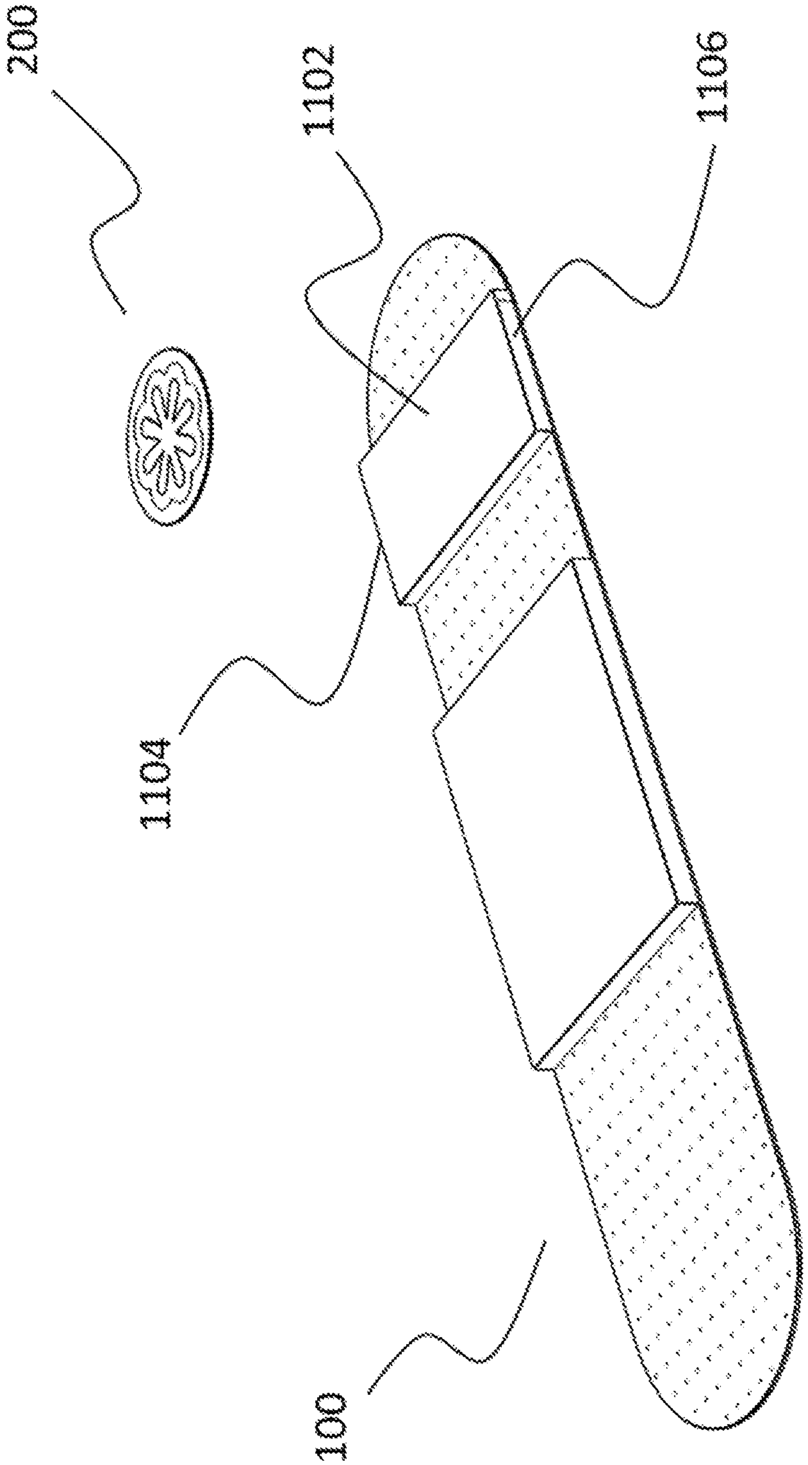
FIG. 11*b* depicts another embodiment of the present device.

As shown in FIG. 11*b*, an alternate embodiment can have a temporary tattoo assembly 200 not running to the edges of a bandage 100, but instead can be fixed to a pad 1102 that can run to the edges of a bandage 100. Temporary tattoo assembly 200 can be affixed to a pad 1102 via double-sided adhesive or any other known, convenient and/or desired device. Double-sided adhesive can either be water-permeable and/or liquid-permeable or applied on a smaller footprint than the contact surface area of a temporary tattoo assembly 200 to facilitate water and/or liquid access to a paper backing layer 702. A pad 1102 can draw water from the outside environment through its exposed faces 1104 and 1106 and can transfer the water to an inset temporary tattoo assembly 200. A pad 1102 can be made of absorbent and soft materials like cotton or sponge, or any other known, convenient and/or desired material.

Figure 11C:
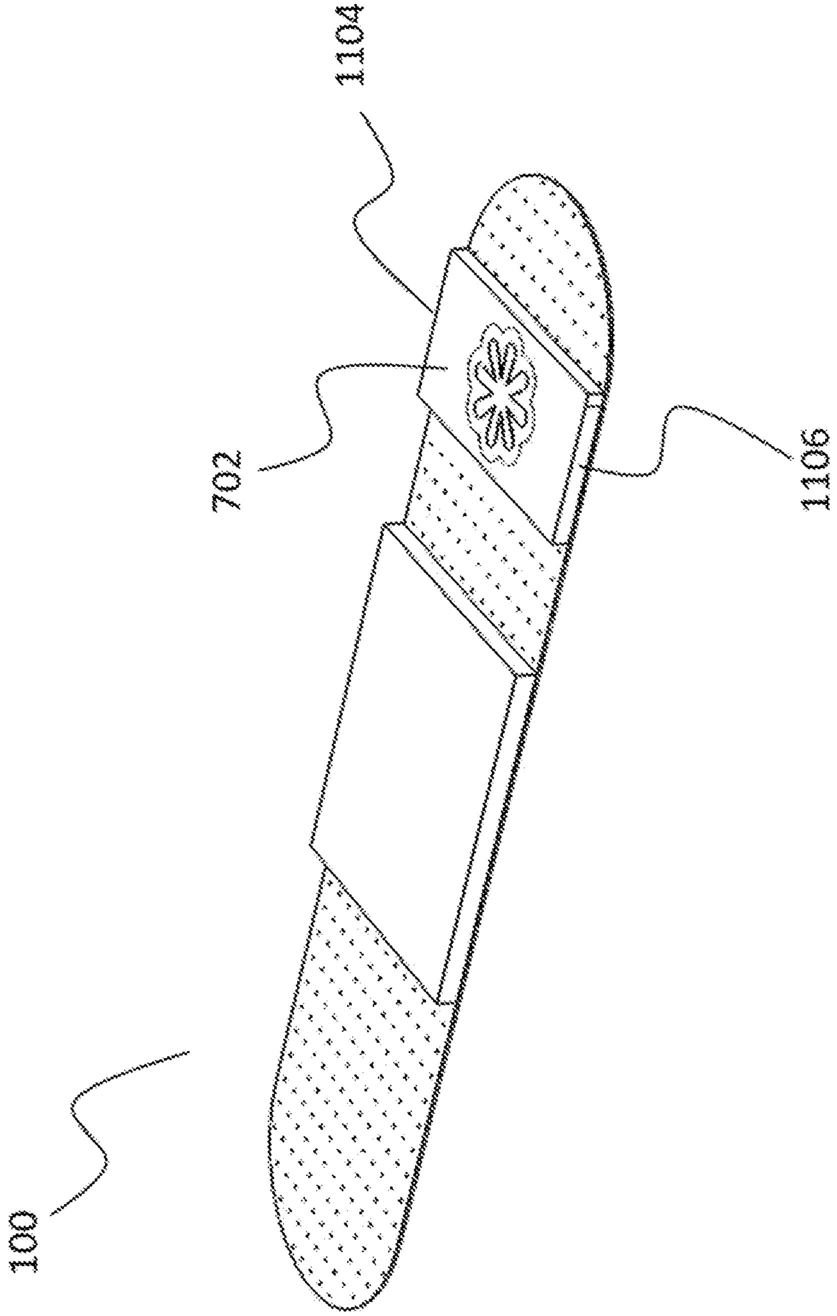
FIG. 11*c* depicts another embodiment of the present device.

FIG. 11*c* depicts another embodiment of the present device. As shown in FIG. 11*b*, a paper backing layer 702 can be made of thicker materials (or assembly of materials) to create larger water/liquid ingress areas 1104 and 1106, and/or made of materials with greater water/liquid absorption.

Figure 11D:
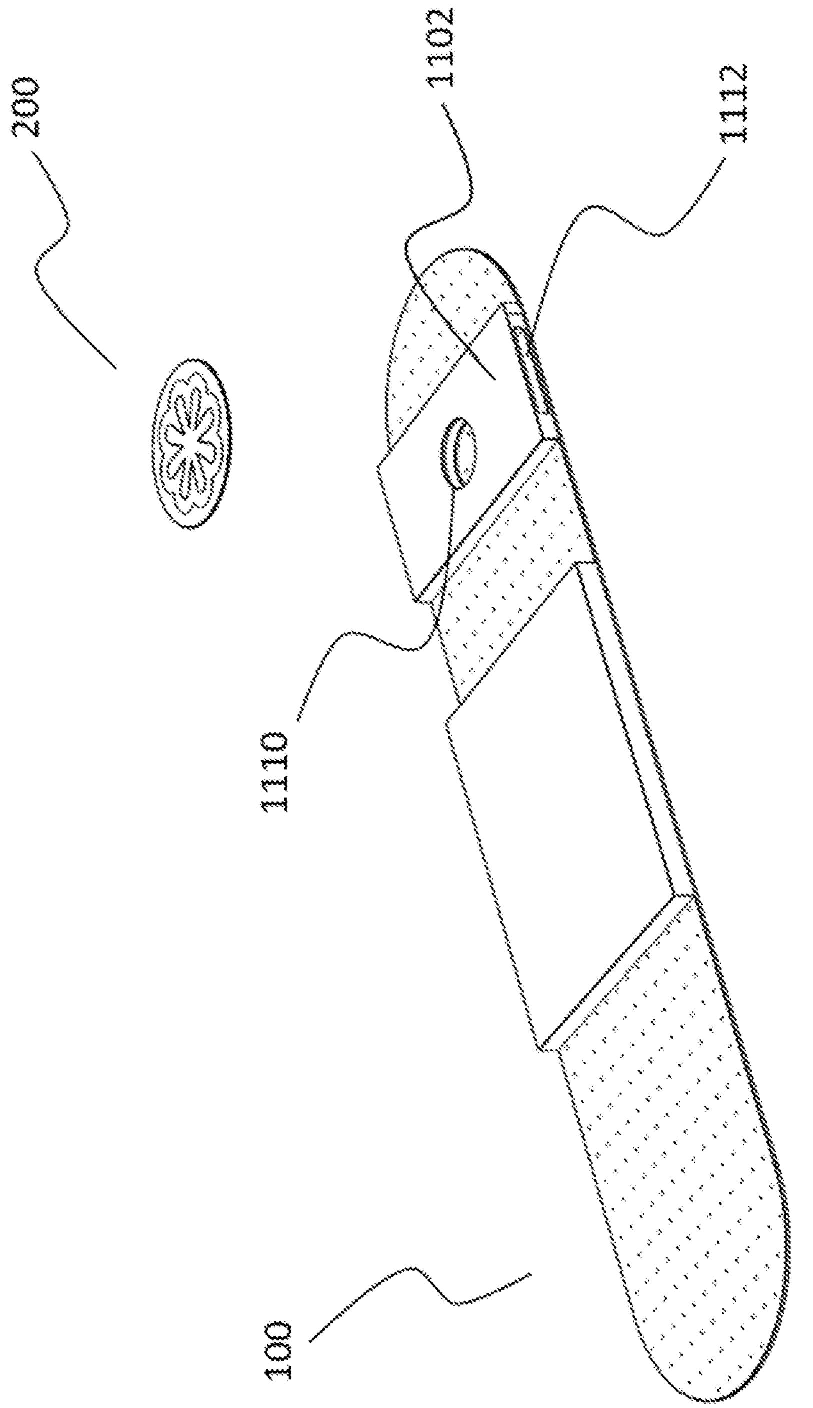
FIG. 11*d* depicts another embodiment of the present device.

FIG. 11*d* depicts another embodiment of the present device. As shown in FIG. 11*d*, a pad 1102 can be designed to create a perpendicular tunnel structure 1110, thereby providing a fluid pathway for the outside water to access the temporary tattoo assembly. A perpendicular tunnel structure 1110 can have a substantially circular geometry, or any other known, convenient and/or desired configuration. Water/liquid can access the temporary tattoo assembly 200 via a perpendicular tunnel structure 1110, or a lateral tunnel structure 1112 on a lateral surface of a pad 1102, or a combination thereof, or by penetrating through the tunnel material wall thickness via absorption. In some embodiments, a lateral tunnel structure 1112 can have a rectangular configuration, but in other embodiments can have any other known, convenient and/or desired configuration.

Figure 11E:
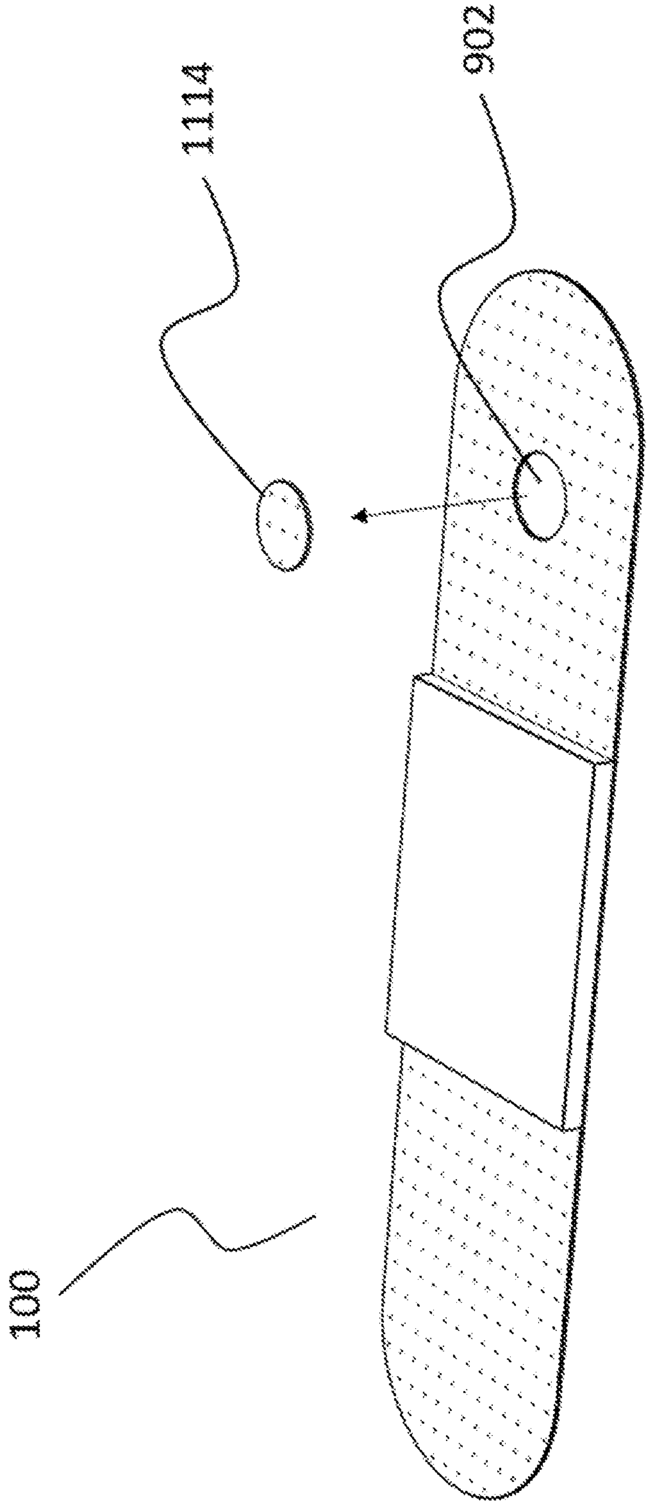
FIG. 11*e* depicts another embodiment of the present device.

FIG. 11*e* depicts another embodiment of the present device. When creating a cutout 902, manufacturers may find it difficult and/or costly to remove the inset bandage material 1114, as shown in FIG. 11*e*, during the manufacturing process in a quick, simple, and reliable manner. It may be advantageous for the manufacturer if all cutouts can be removed simultaneously as a single piece and/or in a single step.

Figure 11F:
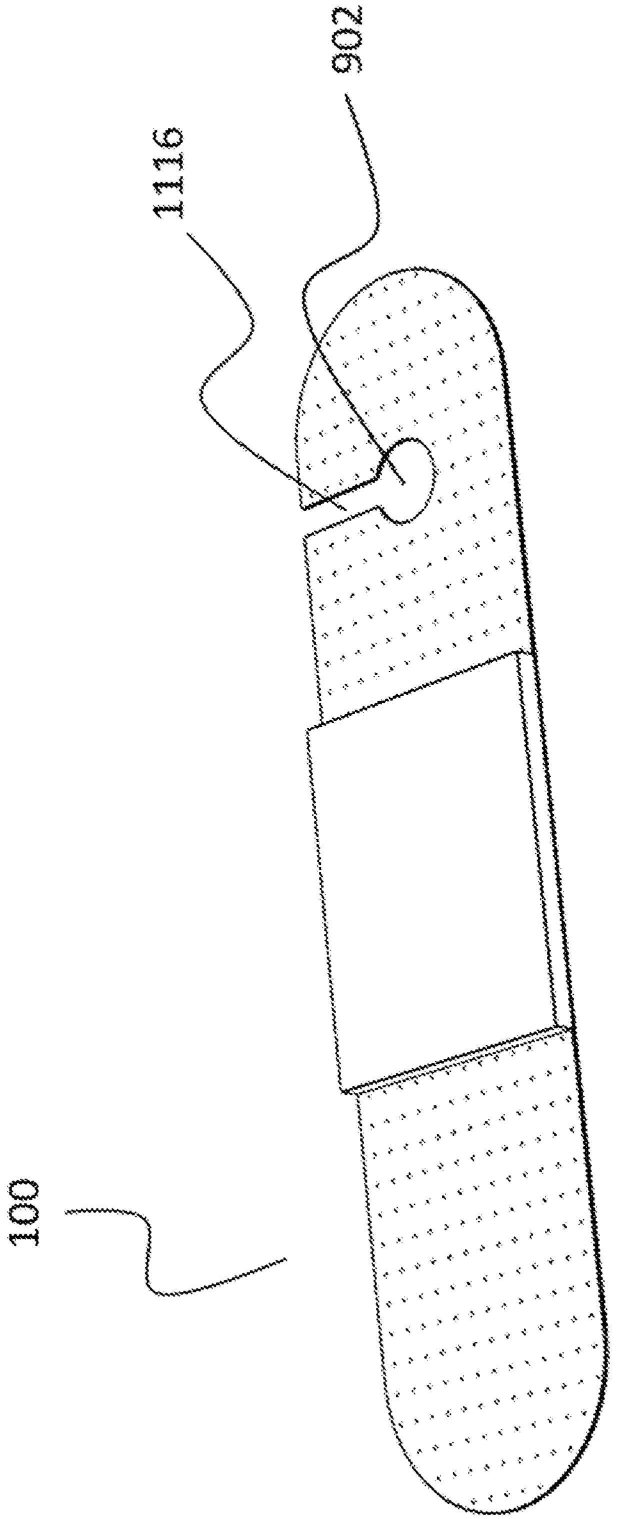
FIG. 11*f* depicts another embodiment of the present device.
Figure 11G:
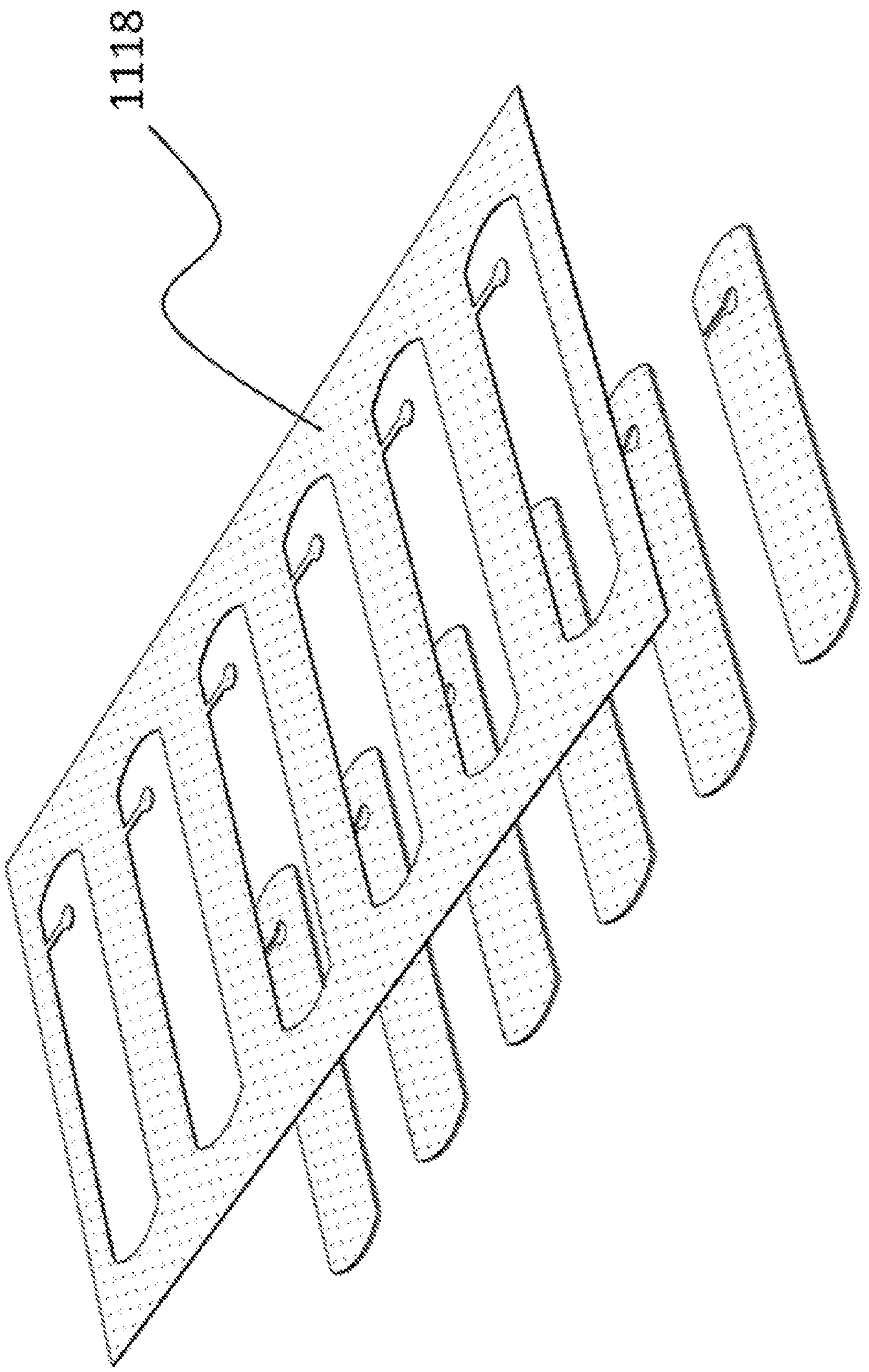
FIG. 11*g* depicts the embodiment shown in FIG. 11*f* in a manufacturing setting.

FIGS. 11*f* and 11*g* depict another embodiment of the present device. In some embodiments, to facilitate manufacturing, a cutout shape 902 can be extended to one of the edges of a bandage 100 via an elongated cutout 1116, as shown in FIG. 11*f*. As shown in FIG. 11*g*, this extension can facilitate cutouts across multiple bandages to be joined as a single piece, facilitating simple removal of all disregarded material 1118. As shown in FIG. 11*f*, an elongated cut out 1116 can be substantially linear and extend to a lateral edge of a bandage 100, but in other embodiments can extend to any other edge of a bandage 100 and have any other known, convenient and/or desired configuration.

Figure 12A:
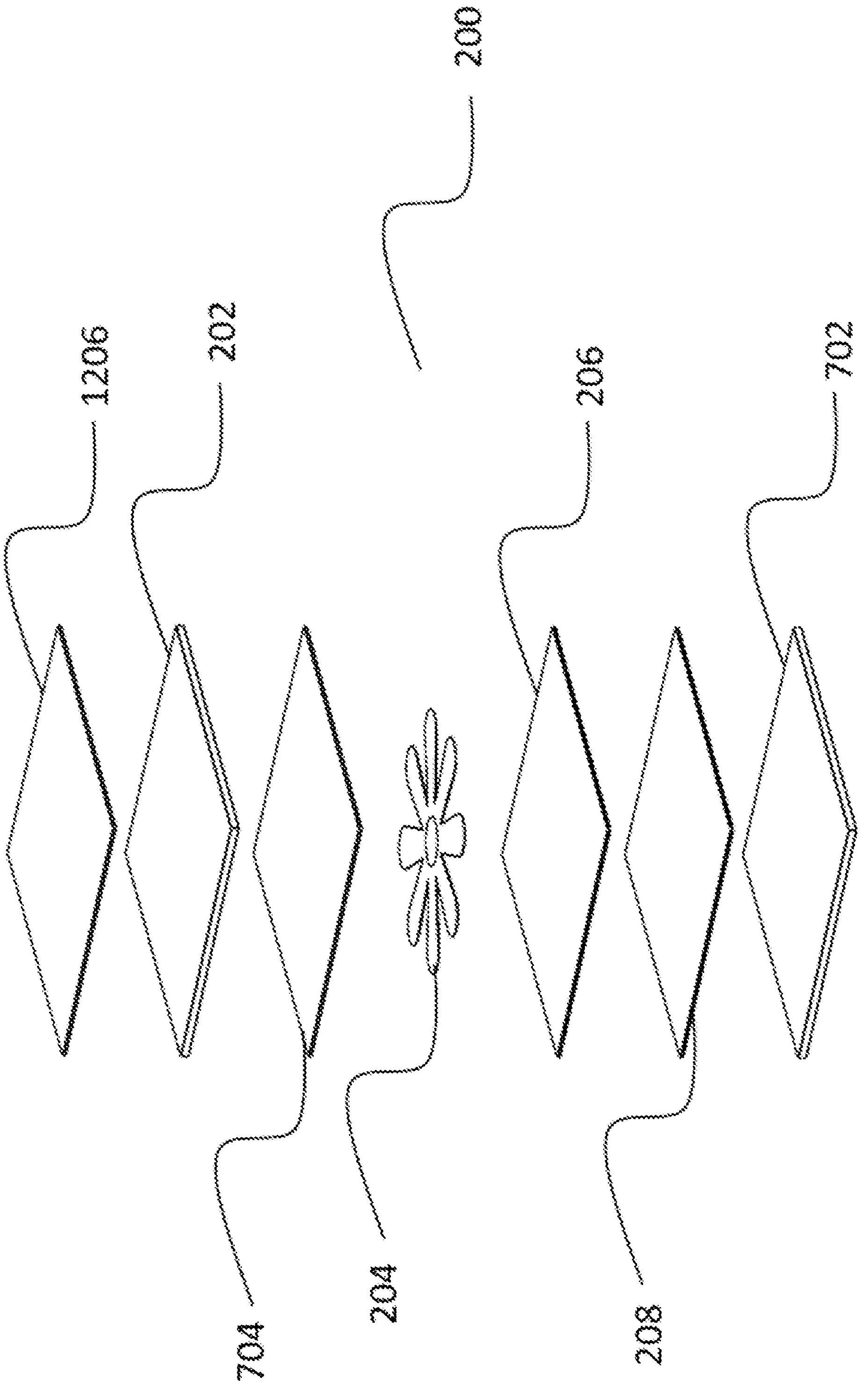
FIG. 12*a* depicts a perspective assembly view of another embodiment of the present device.

FIG. 12*a* depicts a perspective assembly view of another embodiment of the present device. As shown in FIG. 12*a*, a temporary tattoo stand-alone assembly 200 can comprise an adhesive layer 1206 in addition to a cover 202, an adhesive layer 704, an ink layer 204, a transfer layer 206, a release coating 208, and/or a paper backing 702. The outward surface of a cover 202 can comprise an adhesive layer 1206, so the temporary tattoo assembly 200 can be adhered to a protective backing strip 108. In such embodiments, when a backing strip is removed from a bandage 100, a cover 202 can stay with the backing strip 108, while the remainder of a temporary tattoo assembly 200 remains on a bandage 100, with an adhesive layer 704 facing a user's skin 600.

Figure 12B:
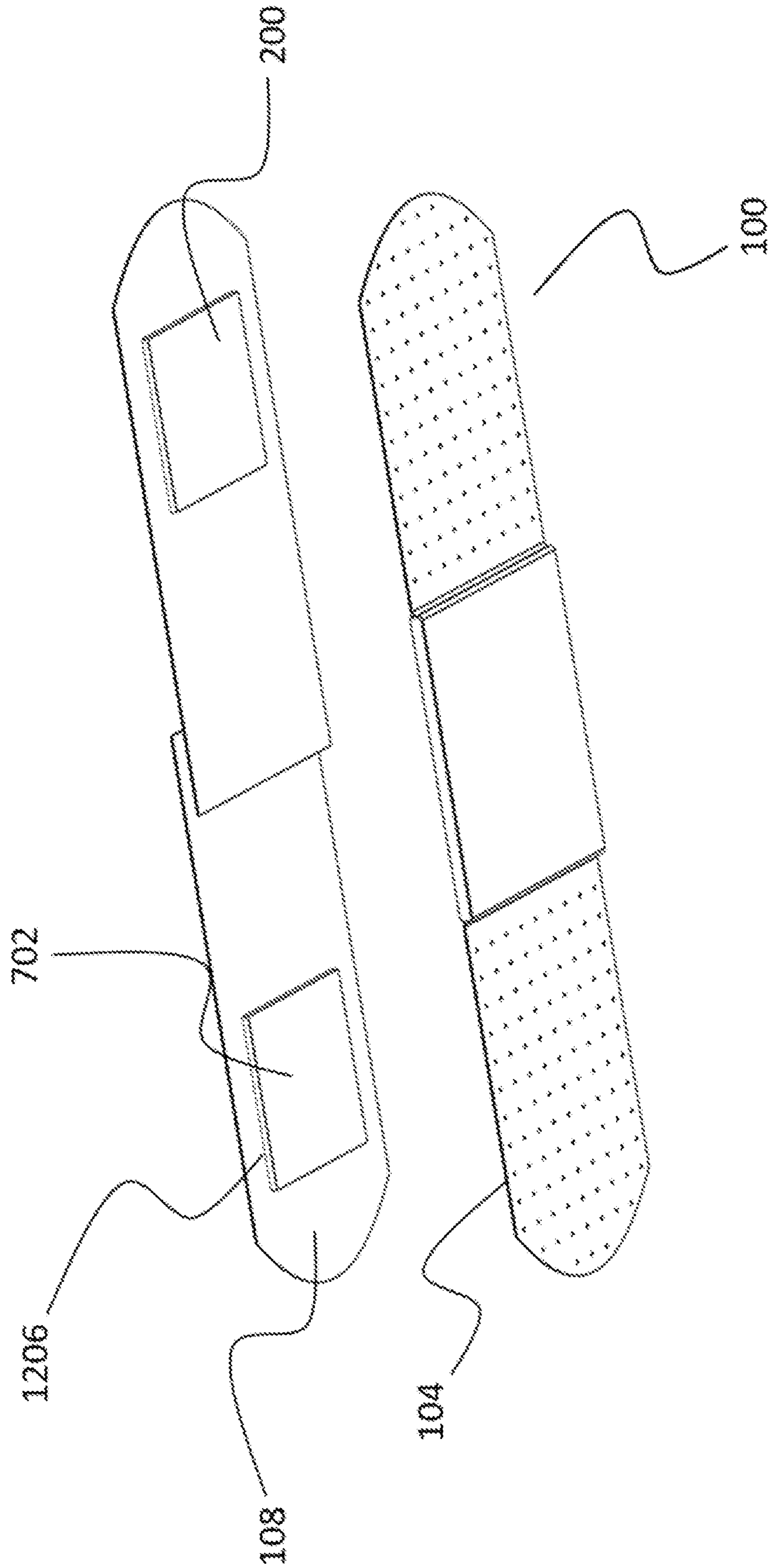
FIG. 12*b* depicts a detailed perspective assembly view of the present device prior to use.

FIG. 12*b* depicts a detailed perspective assembly view of the present device prior to use. As shown in FIG. 12*b*, a tattoo assembly 200 can use the adhesive layer 1206 to adhere to a backing strip 108. In such embodiments, paper backing 702 can face the bandage adhesive layer 104.

Figure 12C:
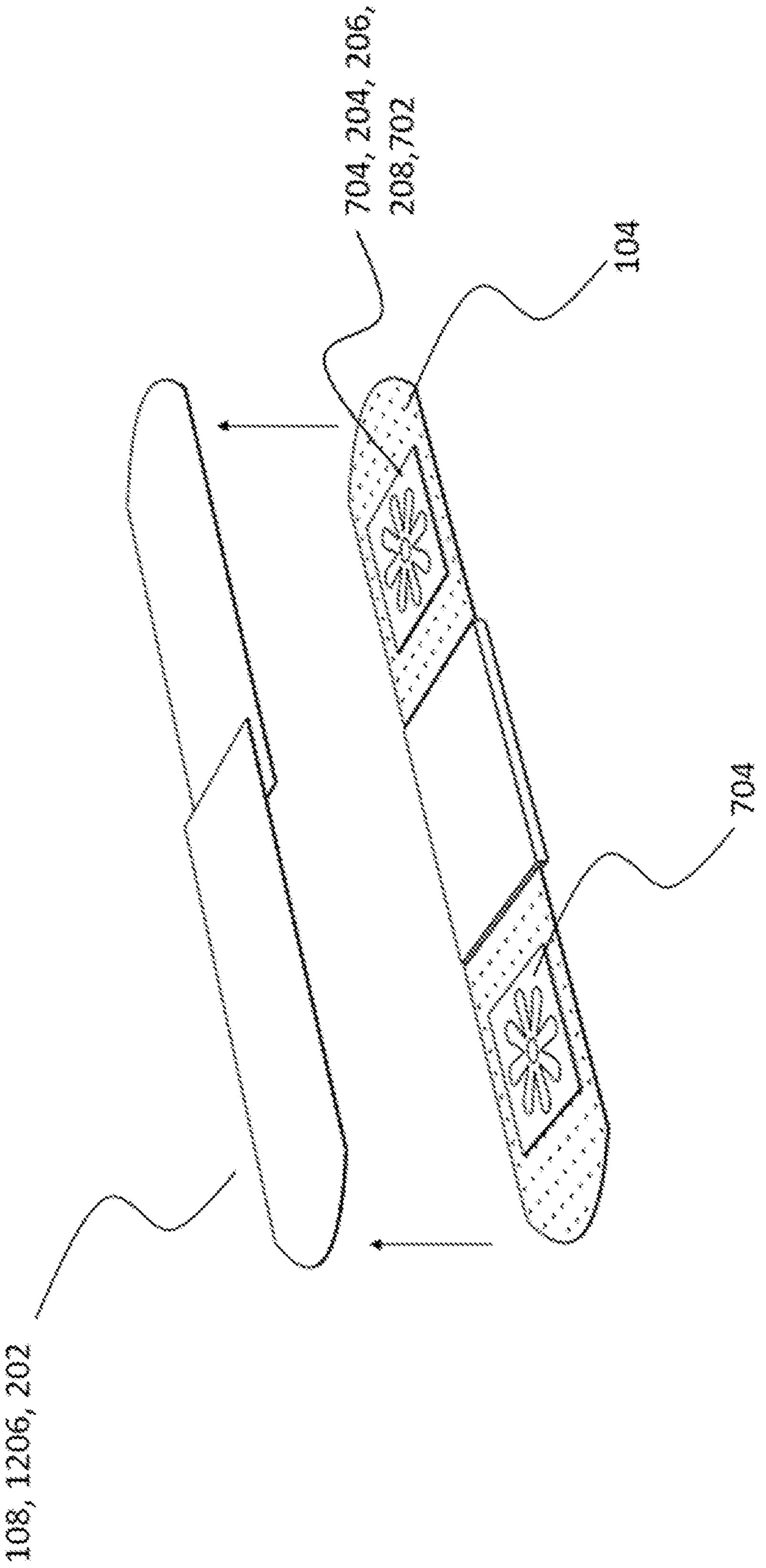
FIG. 12*c* depicts a detailed perspective assembly view of the present device prior to application on a user.

FIG. 12*c* depicts a detailed perspective assembly view of the present device as it can be applied on a user. A backing strip 108 can be removed and carry with it the adhesive layer 1206 and cover 202, exposing an adhesive layer 704, an ink layer 204, a transfer film 206, a release layer 208, and/or a paper backing 702 on a bandage adhesive layer 104. In use, a bandage can be applied to the skin, such that an adhesive layer 704 can be in direct contact with the skin and covered by an ink layer 204, a transfer film 206, a release coating 208, and/or a paper backing 702 under a bandage 100.

Figure 13:
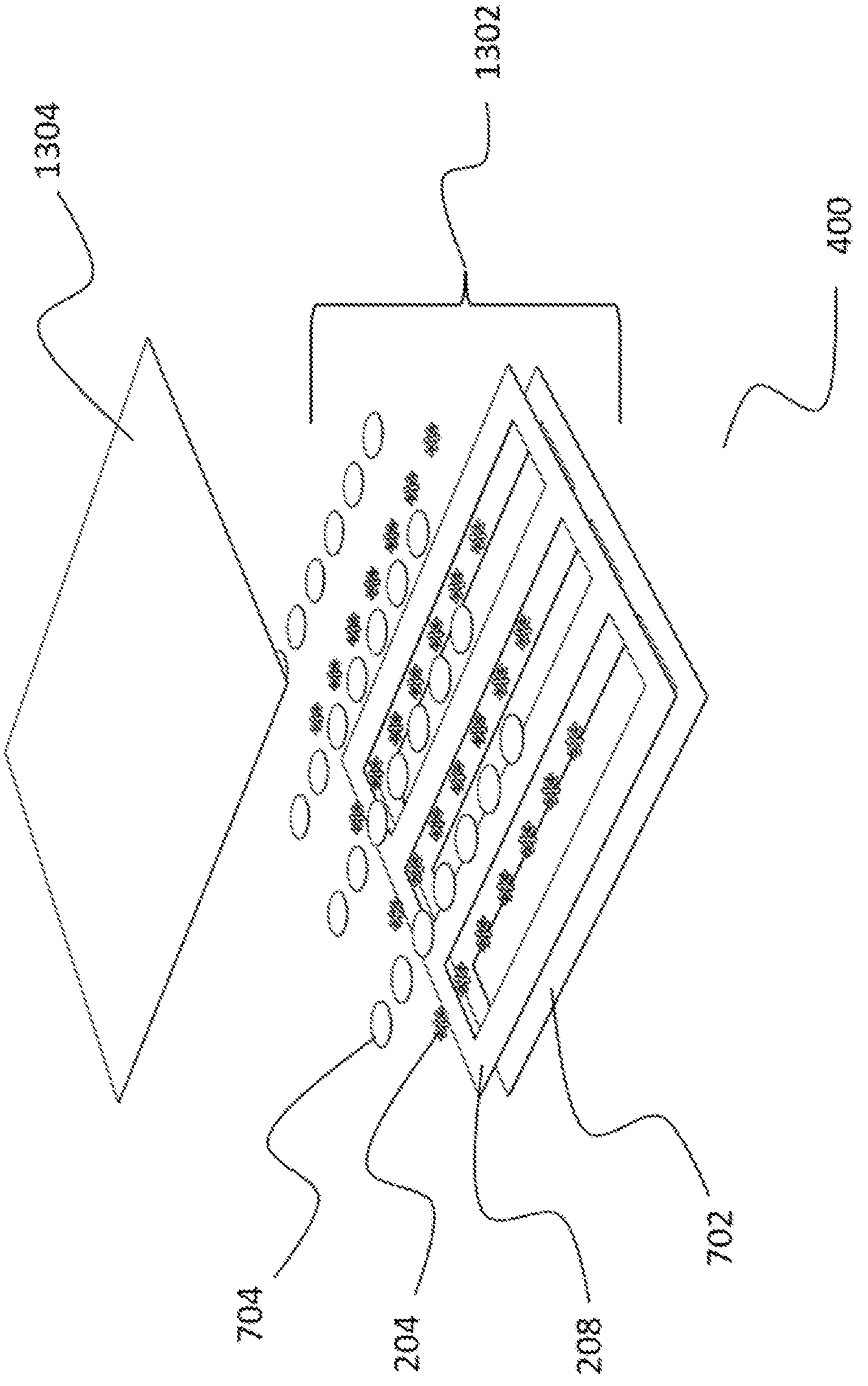
FIG. 13 depicts a perspective assembly view of an embodiment of the present device in manufacturing.

FIG. 13 depicts a perspective assembly view of another embodiment of the sheet 400. In this embodiment, a larger temporary tattoo assembly sheet 1302 (comprised of multiple temporary tattoos) can be adhered to a protective paper 1304, creating a modified protective sheet 400. A temporary tattoo assembly sheet 1302 can be comprised of a double-sided adhesive layer 704, an ink layer 204, a release layer coating 208, and/or a paper backing layer 702. In some embodiments, a transfer film 206 can also be included in the tattoo assembly sheet 1302. In some embodiments, a temporary tattoo assembly sheet 1302 can be oriented relative a protective paper 1304 such that a double-sided adhesive layer 704 can be facing a protective paper 1304. When assembled, a double-sided adhesive layer 704 can be used to hold a temporary tattoo assembly sheet 1302 to a protective paper 1304. In other embodiments, any other known, convenient and/or desired holding methods can be used outside the temporary tattoo areas, such as, but not limited to, additional adhesives, mechanical fittings, and chemical bonds.

In some embodiments, sheet 400 can be inserted into standard manufacturing and assembly machinery. As shown in FIG. 5, a flap cutting pattern 502 for sheet 400 can be the same as for standard protective paper, but now the modified protective flaps can include attached temporary tattoo assemblies 200. Furthermore, modified paper 400 can be custom designed such that a temporary tattoo layout can integrate with any existing or fixed machine cutting pattern. In some embodiments, modified protective sheet 400 can be removably adhered to the adhesive layer 104 side of a sheet of bandage components (a base strip 102, an adhesive layer 104, and a pad 106) to create a sheet of bandage assemblies 100 combined with temporary tattoos 200, which can be cut to any known and or convenient configuration to create a plurality of bandages 100. It will be readily apparent to one of ordinary skill in the art how sheet 400 can alternatively be cut into smaller pieces first and applied individually to bandages already cut to size.

Figure 14A:
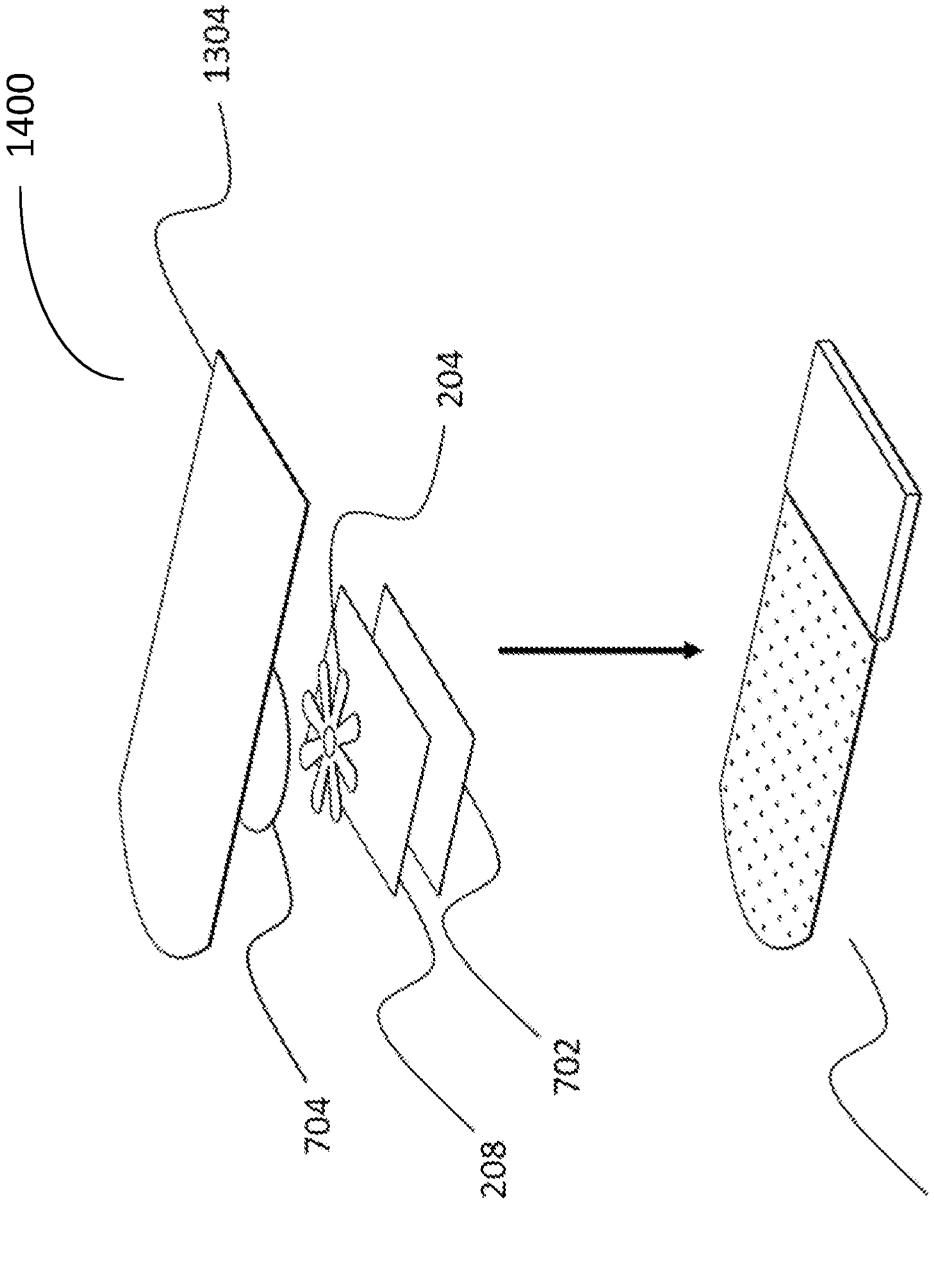
FIG. 14*a* depicts an embodiment of the modified protective paper flap on the present device.

FIG. 14*a* depicts an embodiment of a modified protective paper flap 1400 comprised of the following components: protective paper 1304, double-sided adhesive layer 704, ink layer 204, release coating layer 208, and paper backing 702. Depending on the manufacturer's preference and assembly methods, a wound bandage 100 can comprise one flap with a temporary tattoo and one flap without, or both flaps can include temporary tattoos. The modified flap 1400 can be assembled onto a bandage assembly 100 in a direction and orientation as shown in FIG. 14*a*.

Figure 14B:
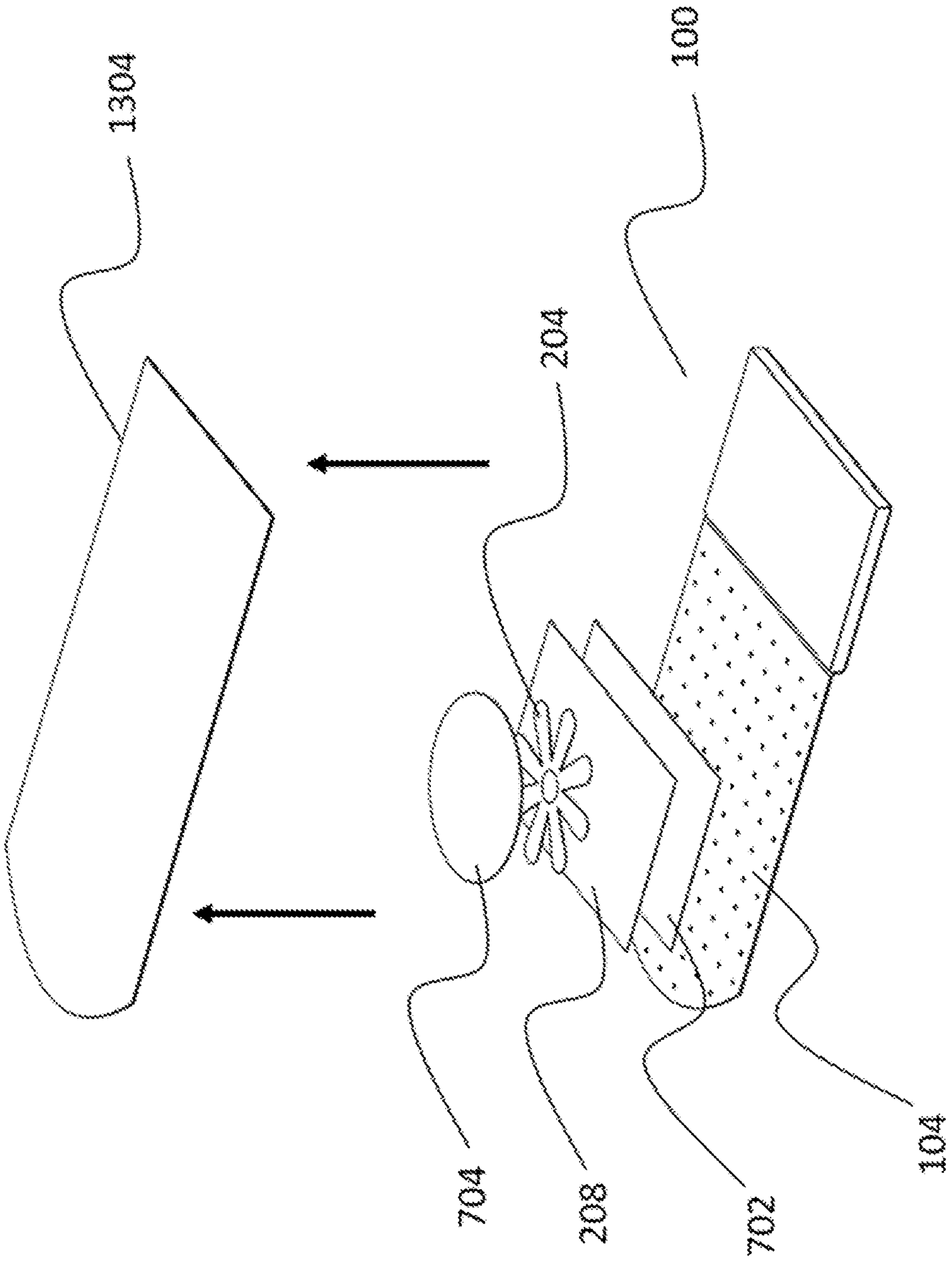
FIG. 14*b* depicts a detailed perspective assembly view of the present device prior to use.

In some embodiments, adhesives may not adhere well to the coated protective paper flap 1304. In such embodiments, a double-sided adhesive 704 can mildly adhere to it. When the modified flap assembly 1400 is lowered onto a bandage assembly 100, a bandage adhesive layer 104 can adhere firmly to the temporary tattoo paper backing 702. A temporary tattoo assembly 200 can be fixed to a bandage assembly 100 and only lightly attached to a paper protective paper 1304. As a result, as shown in FIG. 14*b*, when flap paper 1304 is removed prior to use, the temporary tattoo elements, including adhesive layer 704, ink layer 204, release coating 208, and paper backing layer 702 can remain fixed to a bandage 100 and ready for use.

Figure 15:
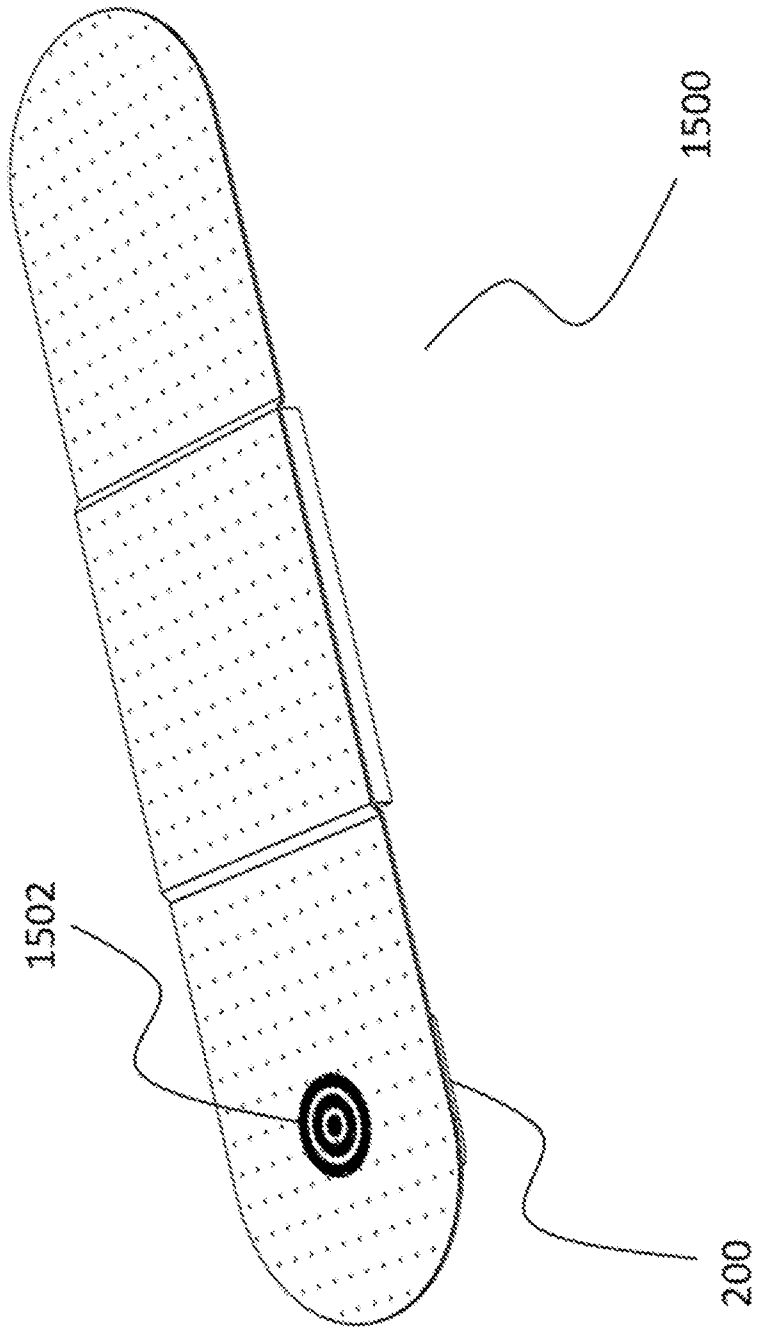
FIG. 15 depicts a perspective view of an embodiment of the present device in use.

FIG. 15 depicts a perspective view of an embodiment of the present device ready for use. As shown in FIG. 15, a temporary tattoo wound bandage product 1500 can have at least one cue 1502 on the outward facing side that sits above a temporary tattoo assembly 200. These cues 1502 can be used to indicate to the user where a temporary tattoo assembly 200 is located on the underside of a temporary tattoo bandage 1500. A cue 1502 can be visual and/or tactile, including but not limited to artwork, surface changes like cutouts or part breaks, material texture differences, or any combination thereof.

During the application of a temporary tattoo bandage 1500, a topside cue 1502 can inform a user where a temporary tattoo assembly 200 is located on the underside, enabling a user to predictably position a temporary tattoo in a desired location on the skin next to a wound. To remove a temporary tattoo bandage 1500 after use, and transfer a temporary tattoo image transfer subassembly 708, a user can apply water or any known, convenient and/or desired liquid to the temporary tattoo assembly 200 area using several methods, including but not limited to, applying a damp cloth or exposing it to running or standing water. A user can apply slight pressure on a temporary tattoo assembly 200 area during and/or after the water application to get a double-sided adhesive 704 to stick to a user's skin and thereby transfer a temporary tattoo ink layer 204 to a user's skin.

Figure 16:
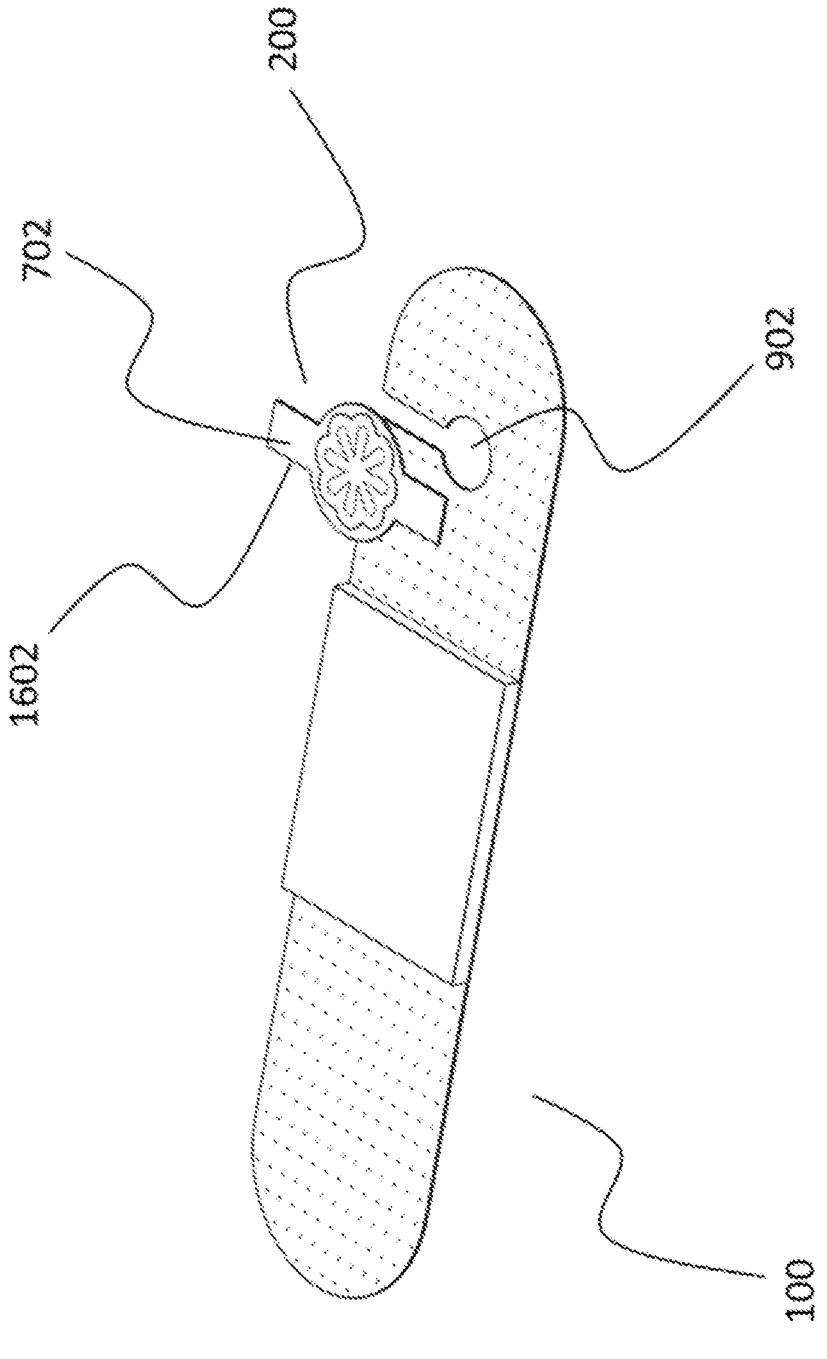
FIG. 16 depicts a perspective detailed view of another embodiment of the present device.

FIG. 16 depicts a perspective, detailed view of another embodiment of the present device. In some embodiments, a paper backing 702 can be substantially similar in size and relative dimensions with the surface area of a temporary tattoo image transfer subassembly 708 while also including at least one segment 1602 extending to at least one edge of a base strip 102 of a bandage 100. In some embodiments, a pair of segments 1602 can extend to opposite lateral edges of a base strip 102, but in alternate embodiments can have any other known, convenient and/or desired configuration. Extending a temporary tattoo paper backing 702 to edges of a bandage 100 can facilitate manufacturing by placing a single continuous strip of temporary tattoos that can extend to multiple bandages, which can be cut when cutting the outer bandage shape as a final step. Further, in such embodiments a paper backing 702 footprint can be minimized and/or selectively designed to maximize a bandage adhesive 104 on a user's skin.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed:

1. An adhesive bandage comprising:

a base strip having an adhesion region and a pad region;

an adhesive layer positioned adjacent to said adhesion region;

a pad positioned adjacent to said pad region;

a protective strip; and a liquid-permeable paper strip;

a liquid-activated release coating adjacent to said liquid permeable paper strip;

wherein said liquid-permeable paper strip is located within said adhesion region;

wherein said liquid-permeable paper strip extends to at least one edge of said adhesion region; and wherein said base strip has at least one aperture in said adhesion region configured to place said liquid-permeable paper strip in fluid communication with a liquid.

2. The adhesive bandage of claim 1, wherein said adhesive layer is configured to bond in a watertight manner with skin.

3. The adhesive bandage of claim 2, further comprising a cut-out within said adhesive layer.

4. The adhesive bandage of claim 3, wherein said temporary tattoo assembly is positioned substantially adjacent to said cut-out.

5. The adhesive bandage of claim 3, further comprising a cut-out through said base strip that extends to an edge of said base strip.

6. The adhesive bandage of claim 1, further comprising:

a temporary tattoo assembly, comprising:

an ink layer;

wherein said ink layer is removably coupled with said liquid-activated release coating.

7. The adhesive bandage of claim 6, wherein said temporary tattoo assembly further comprises a transfer layer.

8. The adhesive bandage of claim 7, wherein the water-permeable paper strip is in direct contact with said transfer layer.

9. The adhesive bandage of claim 6, wherein said temporary tattoo assembly is removably coupled with said liquid-permeable paper strip.

10. The adhesive bandage of claim 9, wherein said liquid-permeable paper strip extends to at least one edge of the base strip.

11. The adhesive bandage of claim 6, wherein said temporary tattoo assembly is removably attached to said adhesion region.

12. The adhesive bandage of claim 6, wherein said temporary tattoo assembly further comprises a second adhesive layer in contact with said ink layer.

13. The adhesive bandage of claim 1, further comprising a cue marker.

14. The adhesive bandage of claim 13 wherein said cue marker is a visually identifiable perimeter of said aperture.

15. The adhesive bandage of claim 1, wherein said liquid-permeable paper strip is integrated within said adhesion region.

16. A combination adhesive bandage and temporary tattoo comprising:

a base strip having an adhesion region and a pad region and having a cutout through said adhesion region of said base strip;

an adhesive layer;

a pad located within said pad region of said base strip;

a protective strip;

a liquid-permeable paper strip;

a liquid-activated coating adjacent to said liquid permeable paper strip; and a temporary tattoo assembly, comprising:

an ink layer; and a second adhesive layer;

wherein said liquid-permeable paper strip is configured to be commensurate with the surface area of said temporary tattoo assembly;

wherein said temporary tattoo assembly is located within said adhesion region of said base strip; and wherein said temporary tattoo assembly is adjacent to said cutout through said adhesion region and is configured to place said temporary tattoo assembly in fluid communication with a liquid.

* * * * *